United States Patent
Buescher et al.

(10) Patent No.: US 9,012,220 B2
(45) Date of Patent: Apr. 21, 2015

(54) CELLS, NUCLEIC ACID CONSTRUCTS, CELLS COMPRISING SAID CONSTRUCTS AND METHODS UTILIZING SAID CELLS IN THE TREATMENT OF DISEASES

(75) Inventors: Dirk Buescher, Madrid (ES); Olga De La Rosa, Madrid (ES); Eleuterio Lombardo, Madrid (ES)

(73) Assignee: Cellerix S.A., Madrid (ES)

( * ) Notice: Subject to any disclaimer, the term of this patent is extended or adjusted under 35 U.S.C. 154(b) by 247 days.

(21) Appl. No.: 13/128,145

(22) PCT Filed: Nov. 6, 2009

(86) PCT No.: PCT/EP2009/064788
§ 371 (c)(1),
(2), (4) Date: Nov. 21, 2011

(87) PCT Pub. No.: WO2010/052313
PCT Pub. Date: May 14, 2010

(65) Prior Publication Data
US 2012/0064031 A1 Mar. 15, 2012

(30) Foreign Application Priority Data
Nov. 7, 2008 (GB) .................................... 0820397.8

(51) Int. Cl.
*C12N 5/077* (2010.01)
*C12N 5/0783* (2010.01)
*C12N 9/02* (2006.01)
*A61K 35/12* (2006.01)

(52) U.S. Cl.
CPC ......... *C12N 5/0653* (2013.01); *A61K 2035/122* (2013.01); *C12N 9/0069* (2013.01); *C12N 2501/70* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 6,451,840 B1 * | 9/2002 | Munn et al. ................... | 514/419 |
| 7,160,539 B2 * | 1/2007 | Munn et al. ................. | 424/93.21 |
| 7,977,093 B2 * | 7/2011 | Groux et al. ................... | 435/326 |
| 8,685,728 B2 * | 4/2014 | Shi et al. ....................... | 435/372 |
| 2003/0194803 A1 * | 10/2003 | Mellor et al. ................... | 435/372 |
| 2008/0155704 A1 * | 6/2008 | Panayi et al. ...................... | 800/3 |
| 2009/0155311 A1 * | 6/2009 | Chen et al. ................... | 424/227.1 |
| 2010/0055111 A1 * | 3/2010 | Sharma et al. ............. | 424/158.1 |
| 2011/0268752 A1 * | 11/2011 | Riley et al. ................. | 424/184.1 |

FOREIGN PATENT DOCUMENTS

| | | |
|---|---|---|
| EP | 1252897 | 10/2002 |
| EP | 1369114 | 10/2003 |
| WO | 2007/039150 | 4/2007 |
| WO | 2007/071053 | 6/2007 |
| WO | 2008/100562 | 8/2008 |

OTHER PUBLICATIONS

Park et al., Arthritis Research & Therapy 2008, 10:R11.*
Li et al., Journal of Investigative Dermatology (2004) 122, 953-964.*
Li et al. (2006) J Invest Dermatol. Jan;126(1):128-136.*
Fallarino et al., Transpl Immunol. Dec. 2006;17(1):58-60.*
Meisel et al., 2004 103: 4619-4621.*
Popp et al., Transplant Immunology 20 (2008) 55-60.*
Yu et al., J Gene Med 2008; 10: 754-761.*
Matysiak et al., Journal of Neuroimmunology 193 (2008) 12-23.*
Prevosto et al.,(2007) Haematologica 92:881-888.*
Di Ianni et al., Experimental Hematology 36:309-318 (2008).*
Guang, et al, Journal of Gene Medicine, 2008; 10: 754-761.
Curti, et al, Blood, 2007; 109: 2871-2877.
De la Rosa: Programme for Conference IFATS08: Symposium 3 "Regulation of lymphocyte proliferation by human adipose-deprived stem cells requires IFN-gamma, IDO activity and generates T cells with suppressor activity" Oct. 23-26, 2008.
Dai, et al., Biochem. Biopys. Res. Comm. 1990; 168(1): 1-8.
Geneseq Database Accession No. ANN62263-X002563367.
Krampera, et al., Current Opinion in Pharmacology 2006; 6: 435-441.
Kang, et al., Stem Cells and Development, 2008; 17: 681-694.
De la Rosa, et al., Tissue Engineering: Part A, 2009; 15(10): 2795-2806.
Peng et al., "Comparative Analysis of Mesenchymal Stem Cells from Bone Marrow, Cartilage, and Adipose Tissue", Stem Cells and Development, 2008, 17:761-774.

* cited by examiner

*Primary Examiner* — Daniel C Gamett
(74) *Attorney, Agent, or Firm* — Klauber & Jackson LLC

(57) ABSTRACT

The present invention relates to cells capable of expressing IDO, nucleic acid constructs for expression of IDO, cells comprising said constructs and methods of utilizing said cells in the treatment of diseases. In particular the present invention relates to cells which express IDO in the absence of exposure to IFN-gamma, and to their use in preparation and/or generation of immunomodulatory cells specific for an antigen.

3 Claims, 6 Drawing Sheets

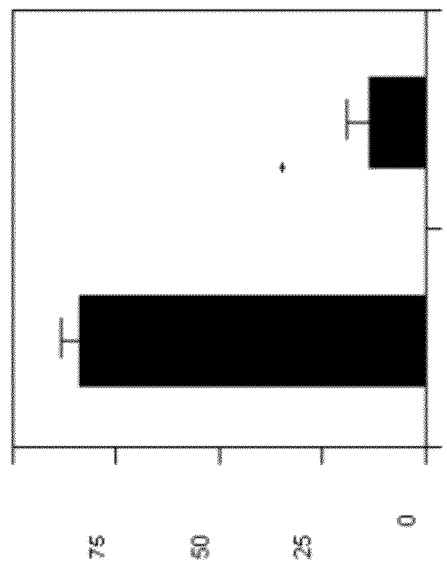
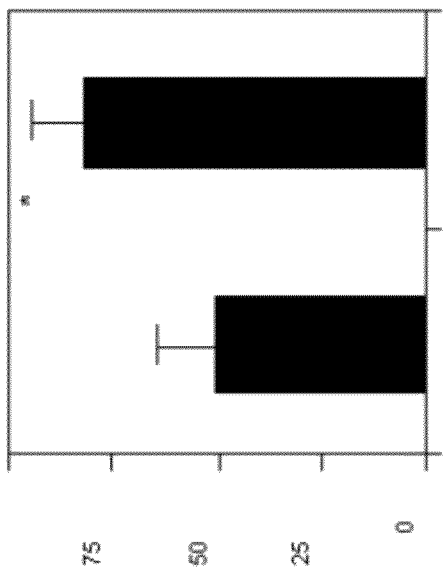
FIGURE 2

CELLS, NUCLEIC ACID CONSTRUCTS, CELLS COMPRISING SAID CONSTRUCTS AND METHODS UTILIZING SAID CELLS IN THE TREATMENT OF DISEASES

CROSS REFERENCE TO RELATED APPLICATIONS

The present application is a National Stage Application claiming the priority of co-pending PCT Application No. PCT/EP2009/064788 filed Nov. 6, 2009, which in turn, claims priority from Great Britain application Serial No. 0820397.8 filed Nov. 7, 2008. Applicants claim the benefits of 35 U.S.C. §120 as to the PCT application and priority under 35 U.S.C. §119 as to the said Great Britain application, and the entire disclosures of both applications are incorporated herein by reference in their entireties.

FIELD OF THE INVENTION

The present invention relates to cells capable of expressing IDO, nucleic acid constructs for expression of IDO, cells comprising said constructs and methods of utilizing said cells in the treatment of diseases.

BACKGROUND OF THE INVENTION

The immune system in higher vertebrates is the first line of defense against various antigens that can enter the vertebrate body, including micro-organisms such as bacteria, fungi and viruses that are the causative agents of a variety of diseases. Moreover, the immune system is also involved in a variety of other diseases or disorders, including autoimmune or immunopathologic diseases, immunodeficiency syndromes, atherosclerosis and various neoplastic diseases. Although methods are available for treating these diseases, many current therapies provide less than adequate results, and carry the risk of significant side effects. Among new emergent therapeutic strategies, those based on cell therapy appear to constitute a potentially useful tool for treating a great number of diseases. Thus, a great effort is currently being made by researchers in order to achieve said aim.

Autoimmune Diseases

Autoimmune diseases are caused when the body's immune system, which is meant to defend the body against bacteria, viruses, and any other foreign product, malfunctions and produces a pathological response against healthy tissue, cells and organs.

T cells and macrophages provide beneficial protection, but can also produce harmful or deadly immunological responses. Autoimmune diseases can be organ specific or systemic and are provoked by different pathogenic mechanisms. Systemic autoimmune diseases involve polyclonal B cell activation and abnormalities of immunoregulatory T cells, T cell receptors and MHC genes. Examples of organ specific autoimmune diseases are diabetes, hyperthyroidism, autoimmune adrenal insufficiency, pure red cell anemia, multiple sclerosis and rheumatic carditis. Representative systemic autoimmune diseases include systemic lupus erythematosus, chronic inflammation, Sjogren's syndrome, polymyositis, dermatomyositis and scleroderina.

Current treatment of autoimmune diseases involves administering immunosuppressive agents such as cortisone, aspirin derivatives, hydroxychloroquine, methotrexate, azathioprine and cyclophosphamide or combinations thereof. The dilemma faced when administering immunosuppressive agents, however, is the more effectively the autoimmune disease is treated, the more defenseless the patient is left to attack from infections, and also the more susceptible for developing tumors. Thus, there is a great need for new therapies for the treatment of autoimmune diseases.

Inflammatory Disorders

Inflammation is a process by which the body's white blood cells and secreted factors protect our bodies from infection by foreign substances, such as bacteria and viruses and is a common process in autoimmune diseases. Secreted factors known as cytokines and prostaglandins control this process, and are released in an ordered and self-limiting cascade into the blood or affected tissues. In general, the current treatments for chronic inflammatory disorders have a very limited efficiency, and many of them have a high incidence of side effects or cannot completely prevent disease progression So far, no treatment is ideal, and there is no cure for these type of pathologies. Thus, there is a great need for new therapies for the treatment of inflammatory disorders.

Inhibition of T-Cell Responses

All immune responses are controlled by T cells. Self-reactive cells with the potential to elicit autoimmune responses comprise a part of the normal T cell repertoire, but in the healthy state, their activation is prevented by suppressor cells. Although T suppressor cells were originally described in the 1970s, significant progress in characterizing T-cell subsets has been made only recently, when they have been renamed as regulatory T cells.

There are different CD4+, CD8+, natural killer cell, and gamma and delta T cell subsets with regulatory (suppressor) activity. Two major types of T-reg cells have been characterized in the CD4+ population, i.e., the naturally-occurring, thymus-generated T-reg cells, and the peripherally-induced, IL-10 or TGF-beta secreting T-reg cells (TrI cells). The CD4+ CD25+, Foxp3-expressing, naturally-occurring T-reg cells generated in thymus, migrate and are maintained in the periphery.

Cell Therapy

Mesenchymal stem cells (MSCs) are multipotent adult stem cells capable of differentiation into mesenchymal-type cells (adipocytes, osteoblasts and chondrocytes), but also myocytes, neurons, endothelial cells, astrocytes and epithelial cells. Although first reported in the normal adult bone marrow (BM-MSC), MSCs can also be obtained from other sources, such as umbilical cord blood, peripheral blood and adipose tissue. Besides the differentiation potential, BM-MSCs have the unique features of being poorly immunogenic and modulating immune responses. Thus, BM-MSCs express low levels of HLA-I, but do not express HLA-II, CD40, CD80 or CD86, allowing BM-MSCs to escape to the immune surveillance. Furthermore, ex-vivo expanded BM-MSCs have been reported to inhibit activation, proliferation and function of immune cells, including T cells, B cells, NK cells and antigen-presenting cells. Despite ample research in recent years, the specific molecular and cellular mechanisms involved in the immunoregulatory activity of BM-MSCs remain controversial. It has been shown that BM-MSCs may modulate T cell phenotype resulting in the generation of cells with regulatory activity. In contrast, soluble factors such as hepatocyte growth factor (HGF), prostaglandin E2 (PGE2), transforming growth factor (TGF)-1, indoleamine 2,3-dioxygenase (IDO), nitric oxide and IL-10 have been implicated. Furthermore, several reports have also shown that inflammatory cytokines such as TNFalpha and IFN gamma may regulate the immunosuppression mediated by MSCs.

The adipose tissue is a source of MSCs referred to as human adipose-derived mesenchymal stem cells (hASC), which can be isolated from liposuctioned fat tissue and expanded over a long time in culture. hASCs share some features with their counterpart in marrow, such as their differentiation potential, low immunogenicity and the ability to suppress immune responses. Recent studies comparing both cell types have reported differences at transcriptional and proteomic levels, suggesting that hASC and BM-MSC, while sharing similarities, are in fact quite different. The specific mechanisms underlying hASCs-mediated immunosuppression have so far been poorly studied. Recently, it has been reported that hASCs may inhibit lymphocyte proliferation by a mechanism that requires, at least in part, the release of PGE2. However, these studies did not provide information regarding (i) other cellular or soluble factors involved in the mechanism of immunosuppression, (ii) the immunosuppressive effect on isolated T cell subsets, or (iii) the phenotypic changes in both hASCs and PBMCs upon co-culture.

These biological abilities make MSCs, including hASCs, an interesting tool for cellular therapy and regeneration. This is further supported by studies showing that BM-MSCs alleviate allograft rejection, graft-versus-host disease, experimental autoimmune encephalomyelitis, collagen-induced arthritis and autoimmune myocarditis. Moreover, it has been recently reported that mouse ASCs (mASCs) were very efficient in protecting against graft-versus-host disease after allogeneic transplantation in an in vivo mouse model. In addition, MSCs are being used in several clinical trials with a focus on their immunomodulatory capacities.

Expression of IDO, a tryptophan catabolizing enzyme, is known to be involved in suppression of T cell proliferation. Moreover, IDO expression seems to be regulated by inflammatory mediators. The involvement of IDO in the mechanism of immunosuppression by professional antigen-presenting cells and BM-MSCs has recently been demonstrated.

SUMMARY OF THE INVENTION

The present invention relates to cells capable of expressing IDO in the absence of IFN-gamma and/or cells that may constitutively express IDO. The invention further relates to nucleic acid constructs comprising polynucleotide sequences encoding the enzyme indoleamine 2,3-dioxygenase or fragments thereof and to cells comprising said construct thereby resulting in the constitutive expression of said enzyme. The present invention further provides methods of utilizing said cells in the preparation and/or generation of cells having immunomodulatory properties. In further aspects the invention provides medicaments and kits comprised of the cells of the invention.

BRIEF DESCRIPTION OF THE FIGURES

FIG. 2 provides two bar charts. Each showing the % of PBMC inhibition on the Y-axis by hASCs-empty on the left hand bar and hASCs-IDO+ on the right hand bar. The bar chart on the left shows the amount of PBMC proliferation at a ratio of 1:50 hASC:PBMC and the bar chart on the right shows the proliferation at a ratio of 1:25 hASC:PBMC.

DEFINITIONS

Figure 1:
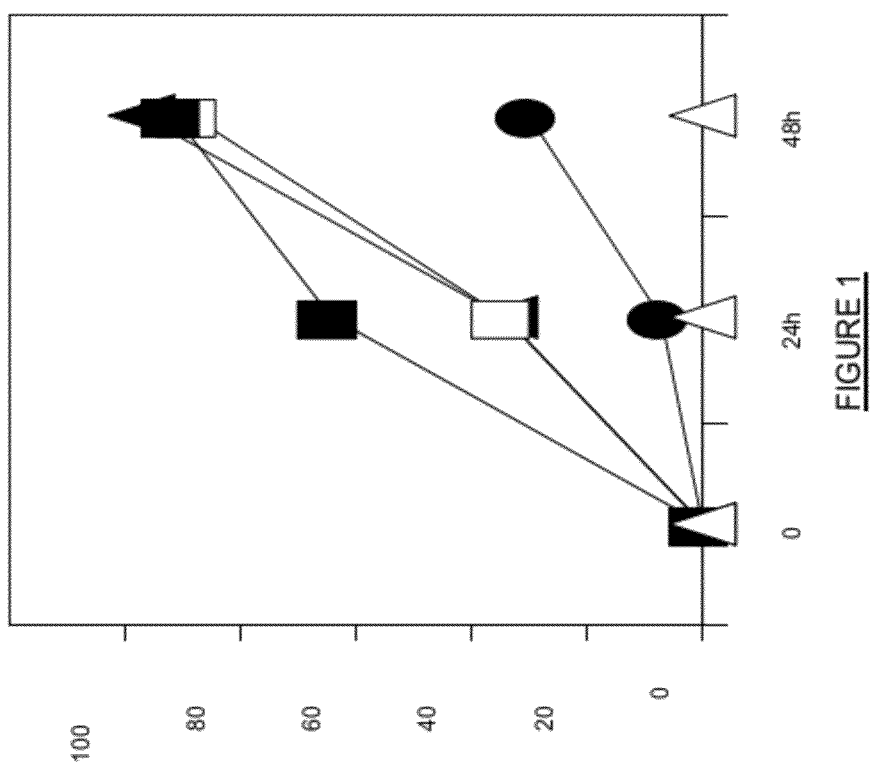
FIG. 1 shows the level of Kynurenine production (Y-axis) in ASCs as measured in mM on the Y-axis at time in hours on the X-axis. Empty triangles refer to hASCs-empty, black triangles refer to hASCs-empty stimulated with IFN-gamma. Empty squares refer to hASCs-IDO+, black squares refer to hASCs-IDO+ stimulated with IFN-gamma. Empty circles refer to hASCs-IDOsi, black squares refer to hASCs-IDOsi stimulated with IFN-gamma.

In order to facilitate the understanding of the present description, the meaning of some terms and expressions in the context of the invention will be explained below. Further definitions will be included along the description when necessary.

The term "IDO" refers to a polypeptide that is an indoleamine 2,3-dioxygenase (INDO; EC 1.13.11.42) or to a polypeptide with substantially similar activity, i.e. a polypeptide that is capable of catalyzing the degradation of the essential amino acid L-tryptophan to N-formyl kynurenine.

The term "allogeneic" as used herein shall be taken to mean from different individuals of the same species. Two or more individuals are said to be allogeneic to one another when the genes at one or more loci are not identical.

The term "autologous" as used herein shall be taken to mean from the same individual.

The term "antigen presenting cells' (APC) refers to a cell population that displays surface foreign antigen complexed with MHC (major histocompatibility complex). Although almost every cell in the body is capable of presenting antigens to T cells, the term "antigen presenting cells' (APC) is herein limited to those specialized cells that express surface MHC II (HLA DP, DQ, DR) and/or MHC I, and include both those in which this expression is induced (for example but not limited to B-cells and CD4 PHA blasts) and also those that are derived from the monocyte-macrophage lineage (for example but not limited to, dendritic cells).

The term "autoimmune disease" refers to a condition in a subject characterized by cellular, tissue and/or organ injury caused by an immunological reaction of the subject to its own cells, tissues and/or organs. Illustrative, non-limiting examples of autoimmune diseases which can be treated with the immunomodulatory cells of the invention include alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, sarcoidosis, scleroderma, progressive systemic sclerosis, Sjogren's syndrome, Good pasture's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, Wegener's granulomatosis, Anti-Glomerular Basement Membrane Disease, Antiphospholipid Syndrome, Autoimmune Diseases of the Nervous System, Familial Mediterranean Fever, Lambert-Eaton Myasthenic Syndrome, Sympathetic Ophthalmia, Polyendocrinopathies, Psoriasis etc.

The term "inflammatory disease" refers to a condition in a subject characterized by inflammation, e.g., chronic inflammation Illustrative, non-limiting examples of inflammatory disorders include, but are not limited to, Celiac Disease, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g., idiopathic pulmonary fibrosis), inflammatory vaculitides (e.g., polyarteritis nodosa, Wegner's granulomatosis, Takayasu's arteritis, temporal arteritis, and lymphomatoid granulomatosus), post-traumatic vascular angioplasty (e.g., restenosis after angioplasty), undifferentiated spondyloarthropathy, undifferentiated arthropathy, arthritis, inflammatory osteolysis, chronic hepatitis, and chronic inflammation resulting from chronic viral or bacteria infections.

The term "isolated' applied to a cell population refers to a cell population, isolated from the human or animal body, which is substantially free of one or more cell populations that are associated with said cell population in vivo or in vitro.

The term "MHC" (major histocompatibility complex) refers to a subset of genes that encodes cell-surface antigen-presenting proteins. In humans, these genes are referred to as human leukocyte antigen (HLA) genes. Herein, the abbreviations MHC or HLA are used interchangeably.

The term "subject" refers to an animal, preferably a mammal including a non-primate (e.g., a cow, pig, horse, cat, dog, rat, or mouse) and a primate (e.g., a monkey, or a human). In a preferred embodiment, the subject is a human.

The term "immunomodulatory" refers to the inhibition or reduction of one or more biological activities of the immune system. The term "antigen specific immunomodulatory" refers to the inhibition or reduction of one or more biological activities of the immune system associated with a specific antigen or antigens, including both alloantigens and autoantigens. The term "immunomodulatory" shall be taken to comprise "antigen specific immunomodulatory".

The terms "immunomodulatory agent", "immunomodulatory cell population", "immunomodulatory cell" or "immunomodulatory cells" as used herein shall be taken to mean agents, cell(s) or populations thereof that inhibit or reduce one or more biological activities (for example but not limited to, the proliferation, differentiation, priming, effector function, production of cytokines or expression of antigens) of one or more immune cells (for example but not limited to T cells).

The term "T-cell" refers to cells of the immune system which are a subset of lymphocytes that express the T cell receptor (TCR). The term "regulatory T-cells" (also referred to herein as T-reg cells) refers to T cell subsets that actively suppress activation of the immune system and prevent pathological self-reactivity, ie an autoimmune disease. The term "regulatory T-cells" or "T-reg cells" shall be taken to include both naturally occurring T-cells (also known as $CD4^+CD25^+FoxP3^+$ T-reg cells) and adaptive T-cells (also known as Tr1 cells or Th3 cells) which do not express the FoxP3 molecule.

In a particularly preferred embodiment of the present method said immunomodulatory agents, cell(s) or populations thereof are regulatory T-cells, however in an alternative embodiment of the method they may be cells of other phenotypes that have been modified such that they are capable of performing the immunosuppressive functions of regulatory T-cells. For example, cells of other phenotypes may have previous to said modification lacked one or more of the following capabilities: suppression of a mixed lymphocyte reaction; suppression of a cytotoxic T cell response; inhibition of DC maturation; inhibition of T cell production of inflammatory cytokines.

As used herein, "negative" or "−" as used with respect to cell surface markers shall be taken to mean that mean that, in a cell population, less than 20%, 10% or less, preferably 9% or less, 8% or less, 7% or less, 6% or less, 5% or less, 4% or less, 3% or less, 2% or less, 1% or less or none of the cells express said marker. Expression of cell surface markers may be determined for example by means of flow cytometry for a specific cell surface marker using conventional methods and apparatus (for example a Becton Dickinson FACS Calibur system used with commercially available antibodies and standard protocols known in the art).

As used herein the term mesenchymal stem cell (also referred to herein as "MSC") shall be taken to mean a multipotent cell type originally derived from the mesenchyme. The term "stem cell" shall be taken to mean a cell that, by successive divisions, can give rise to specialised cells. Multipotent stem cells can give rise to multiple types of specialized cells.

As used herein, the expression "significant expression" or its equivalent terms "positive" and "+" when used in regard to a cell surface marker shall be taken to mean that, in a cell population, more than 20%, preferably, 30% or more, 40% or more, 50% or more, 60% or more, 70% or more, 80% or more, 90% or more or all of the cells express said marker.

Expression of cell surface markers may be determined for example by means of flow cytometry for a specific cell surface marker using conventional methods and apparatus (for example the Becton Dickinson FACS Calibur system used with commercially available antibodies and standard protocols known in the art) that show a signal for a specific cell surface marker in flow cytometry above the background signal using conventional methods and apparatus (for example a Becton Dickinson FACS Calibur system used with commercially available antibodies and standard protocols known in the art). The background signal is defined as the signal intensity given by a non-specific antibody of the same isotype as the specific antibody used to detect each surface marker in conventional FACS analysis. For a marker to be considered positive the specific signal observed is stronger than 20%, preferably, stronger than 30%, stronger than 40%, stronger than 50%, stronger than 60%, stronger than 70%, stronger than 80%, stronger than 90%, stronger than 500%, stronger than 1000%, stronger than 5000%, stronger than 10000% or above, than the background signal intensity using conventional methods and apparatus (for example a Becton Dickinson FACS Calibur system used with commercially available antibodies and standard protocols known in the art).

Furthermore, commercially available and known monoclonal antibodies against cell-surface and/or intracellular markers (e.g., cellular receptors and transmembrane proteins) can be used to identify relevant cells.

The term "connective tissue" refers to tissue derived from mesenchyme and includes several tissues which are characterized in that their cells are included within the extracellular matrix. Examples of connective tissues include but are not limited to, adipose and cartilaginous tissues.

The term "fibroblast" as used herein shall be taken to include fibroblast like synovial cells.

The term "gluten" shall be taken to mean a protein comprising of gliadin and glutenin components.

The term "vector" or "nucleic acid vector" shall be taken to mean an agent (commonly a DNA molecule) that can carry a foreign DNA fragment into a host or recipient cell.

The term "cloning vector" shall be taken to mean a vector that carries foreign DNA into a host cell, replicates said cell and produces many copies of itself and the foreign DNA.

The term "expression vector" shall be taken to mean a vector that enables expression of the foreign DNA fragment in the host or recipient cell.

As used herein, the terms "treat", "treatment" and "treating" when used directly in reference to a patient or subject shall be taken to mean the amelioration of one or more symptoms associated with a disorder including, but not limited to, an inflammatory disorder, an autoimmune disease or an immunologically mediated disease including rejection of transplanted organs and tissues, wherein said amelioration results from the administration of the immunomodulatory cells of the invention, or a pharmaceutical composition comprising thereof, to a subject in need of said treatment.

DETAILED DESCRIPTION OF THE INVENTION

The present invention relates to cells capable of expressing IDO in the absence of IFN-gamma and cells that may constitutively express IDO. These cells allow for the first time for expression of IDO in the absence of an inducer such as IFN-gamma. Without being bound by theory the present invention thus allows for the use of IDO in immunosuppression in cellular therapy, without the initial involvement of inflammatory mediators.

The invention further relates to nucleic acid constructs comprising polynucleotide sequences encoding the enzyme indoleamine 2,3-dioxygenase or fragments thereof and to cells comprising said construct thereby resulting in the constitutive expression of said enzyme. The present invention further provides methods of utilizing said cells in the preparation and/or generation of cells having immunomodulatory properties. In further aspects the invention provides medicaments and kits comprised of the cells of the invention.

Nucleic Acid Constructs of the Invention

In a first aspect the present invention provides a nucleic acid expression construct comprising i) at least one polynucleotide encoding indoleamine 2,3-dioxygenase or protein fragments retaining the functionality thereof. In a further embodiment said polynucleotide may comprise a plurality of segments encoding indoleamine 2,3-dioxygenase or protein fragments retaining the functionality thereof, wherein said segments are arranged consecutively but each of said segments may be separated from the next by one or a plurality of nucleotides.

Preferably said polynucleotide is at least 800, at least 900, at least 1000, at least 1100, or at least 1200 nucleotides in length.

In one embodiment said nucleic polynucleotideencoding indoleamine 2,3-dioxygenase or fragments thereof comprises a polynucleotide encoding the IDO protein sequence as disclosed in SEQ ID NO: 5, or proteins having at least at least 90%, at least 95%, at least 96%, at least 97%, at least 98% or at least 99% homology thereto. SEQ ID NO: 5 discloses the indoleamine 2,3-dioxygenase amino acid sequence.

In one embodiment said nucleic polynucleotide encoding indoleamine 2,3-dioxygenase or fragments thereof comprises of at least 800, at least 900, at least 1000, at least 1100, or at least 1200 nucleotides of SEQ ID NO: 1 or SEQ ID NO: 6. In order to account for the redundancy of the genetic code this shall be taken to include functionally equivalent fragments, variants, and analogs of said nucleic acids. Therefore this shall be taken to include sequences having at least 95%, at least 96%, at least 97%, at least 98% or at least 99% homology with SEQ ID NO: 1 or with SEQ ID NO: 6. SEQ ID NO: 1 and SEQ ID NO: 6 each disclose cDNA sequences encoding functional indoleamine 2,3-dioxygenase amino acid sequences.

In a further aspect said nucleic acid expression construct further comprises at least one further polynucleotide encoding a promoter for directing the expression of said first polynucleotide.

It is particularly preferred that said promoter is a constitutive promoter. It is preferred that said promoter is a viral or eukaryotic promoter. Particularly preferred is a eukaryotic promoter. In a further embodiment said promoter may be selected form the group consisting of CMV promoter, HSV promoter, viral LTR, HIV promoter, chicken actin promoter.

Said nucleic acid expression constructs will hereinafter be referred to as the nucleic acid constructs of the invention. Methods for the preparation of the nucleic acid constructs of the invention are known in the art.

The nucleic acid constructs of the present invention are suitable for use in the production of the enzyme indoleamine 2,3-dioxygenase by means of insertion into recipient cells, thereby enabling said recipient cells to constitutively produce said enzyme or functionally equivalent fragments, variants, or analogs thereof. Therefore in one embodiment the present invention provides a cell comprising an exogenous nucleic acid construct of the invention. The nucleic acid construct of the invention may in a further aspect of the invention be inserted into a suitable nucleic acid vector (hereinafter referred to as a "vector"), to enable isolation, amplification and/or insertion into the host or recipient cell or genome thereof. Such vectors include but are not limited to expression vectors and cloning vectors, such as but not limited to plasmids, hybrid plasmids, cosmids, phage vectors, viral vectors, bacterial artificial chromosomes and yeast artificial chromosomes. The person skilled in that art is capable of selecting an appropriate vector having regard to factors including the size of nucleic acid construct and type of recipient cell.

Accordingly in a further aspect the invention provides a vector comprising a nucleic acid construct of the invention. It is preferred that said vector is selected form the group consisting of plasmids, hybrid plasmids, cosmids, phage vectors, viral vectors, bacterial artificial chromosomes and yeast artificial chromosomes. Most preferably said vectors are a plasmid, cosmid or viral vector.

In one embodiment said recombinant nucleic acid expression construct of the invention inserted into a vector comprises of, or essentially of SEQ ID NO: 2.

The vector comprising the nucleic acid may be used for insertion of the nucleic acid construct of the invention into a host or recipient cell. Wherein the vector is a cloning vector it is particularly preferred that said host or recipient cell is a monocellular organism (for example but not limited to bacterial or yeast cell) or other microorganism suitable for use in the cloning of foreign DNA.

Wherein the vector is an expression vector it is particularly preferred that said host or recipient cell is an animal cell, preferably mammalian cells, and are more preferably homo sapiens cells. It is particularly preferred that said recipient cells are mesenchymal stem cells, fibroblast cells or fibroblast like synovial cells. It is further preferred that said recipient cells are of postnatal origin, and may be isolated from any tissue suitable therefore, for example but not limited to bone marrow, connective tissue, adipose, umbilical cord, cord blood and placenta. In a particularly preferred embodiment said recipient cells are stem cells derived from adipose tissue. Said adipose may be of any suitable origin, however particularly preferred are subcutaneous adipose tissue or organ associated adipose tissue (for example but not limited to adipose associated with the heart, liver, kidneys or pancreas).

Cells comprising the nucleic acid constructs of the invention and constitutively expressing indoleamine 2,3-dioxygenase have in vivo immunoregulatory capabilities suitable for the therapy of patients in need thereof. Accordingly the present invention provides cells transfected or transformed with the nucleic acid construct of the invention. The invention also provides a cell comprising a nucleic acid construct of the invention and constitutively expressing IDO or functionally equivalent fragments, variants, and analogs thereof.

The exogenous nucleic acid construct may be integrated into the genome or other endogenous genetic matter of the recipient cell either stably or non-stably, or may be contained within the cell but discrete from the endogenous genetic matter thereof.

Cells comprising the nucleic acid constructs of the present invention are hereinafter referred to as "IDO cells of the invention". IDO cells of the invention are capable of expressing IDO in the absence of exposure to IFN-gamma and/or constitutively express IDO. Particularly preferred are IDO cells of the invention expressing indoleamine 2,3-dioxygenase. It is particularly preferred that said cells secrete Kynurenine. Further preferred are IDO cells of the invention expressing and secreting indoleamine 2,3-dioxygenase wherein said cells are undifferentiated and/or multipotent stem cells.

Methods for Preparing IDO Cells of the Invention

In one aspect the present invention provides methods for preparing IDO cells of the invention. Said method comprises introducing the nucleic acid constructs of the present invention into an isolated viable recipient cell or cells.

Said recipient cells may be animal or human cells but are preferably mammalian cells, and are more preferably homo sapiens cells. It is particularly preferred that said recipient cells are mesenchymal stem cells (hereinafter also referred to as MSC), fibroblast cells or fibroblast like synovial cells. It is further preferred that said recipient cells are of post-natal origin and may be isolated from any tissue suitable therefore, for example but not limited to bone marrow, adipose, umbilical cord, cord blood and placenta. The recipient MSC used in the method of the present invention are preferably derived from connective tissue. In an alternative embodiment, said recipient MSC are obtained from chondrocytes of the hyaline cartilage. In a further embodiment, said recipient MSC are obtained from skin. In another embodiment, said recipient MSC are obtained from bone marrow.

In the most preferred embodiment said recipient MSC are derived from adipose tissue and in a further preferred embodiment from the stromal fraction of the adipose tissue. In a particularly preferred embodiment said recipient cells are stem cells derived from adipose tissue. Said adipose may be of any suitable origin, however particularly preferred are subcutaneous origin or organ associated adipose tissue (for example but not limited to adipose associated with the heart, liver, kidneys or pancreas).

Any suitable methods for the harvesting of adipose tissue from a subject may be used, and include but are not limited to lipoaspiration, liposuction and biopsy. The person skilled in the art will be versed in methods for the isolation of mesenchymal stem cells from adipose sources. Such methods are known in the art, and protocols for such isolation are easily available. Briefly, the adipose matter is first washed (using for example but not limited phosphate-buffered saline) and then enzymatically digested to obtain a cell suspension, e.g. using collagenase. The cells are then isolated from the suspension e.g. by centrifugation and resuspension in an appropriate buffer or growth medium. The isolated cell population is termed the stromal vascular fraction, and mesenchymal stem cells may be isolated therefrom on the basis of their adherent characteristics.

Wherein the recipient cells are mesenchymal stem cells (hereinafter referred to as MSC) it is preferred that they are negative for markers associated with APC phenotypes. Accordingly it is preferred that said recipient MSC are negative for at least one, two, three, four or preferably all of the following markers CD11b; CD11c; CD14; CD45; HLAII. Furthermore, the recipient MSC are preferably negative for at least one, two, or preferably all of the following cell surface markers CD31; CD34; CD133.

In a particular embodiment, the recipient MSC as used in the present method are preferably characterised in that they express (i.e. are positive for) at least one, two, three, four, of or preferably all of the following cell surface markers CD9, CD44, CD54, CD90 and CD105. Preferably, the recipient MSC are characterised in that they have significant expression levels of at least one, two, three, four, of and preferably all of said cell surface markers (CD9, CD44, CD54, CD90 and CD 105).

Optionally, the recipient MSC may also be negative for the cell surface marker CD106 (VCAM-1). Examples of recipient MSC suitable for use in the method of the present invention are described in the art, for example in WO2007039150 which is hereby incorporated by reference in its entirety.

Recipient MSC

The recipient MSC suitable for use in the method of the present invention may present the capacity to proliferate and be differentiated into at least two, more preferably three, four, five, six, seven or more cell lineages. Illustrative, non-limiting examples of cell lineages into which said recipient MSC can be differentiated include osteocytes, adipocytes, chondrocytes, tenocytes, myocytes, cardiomyocytes, hematopoietic-supporting stromal cells, endothelial cells, neurons, astrocytes, and hepatocytes. Recipient MSC can proliferate and differentiate into cells of other lineages by conventional methods. Methods of identifying and subsequently isolating differentiated cells from their undifferentiated counterparts can be also carried out by methods well known in the art.

Recipient MSC are also capable of being expanded ex vivo. That is, after isolation, said MSC can be maintained and allowed to proliferate ex vivo in culture medium. Such medium is composed of, for example, Dulbecco's Modified Eagle's Medium (DMEM), with antibiotics (for example, 100 units/ml Penicillin and 100 [mu]g/ml Streptomycin) or without antibiotics, and 2 mM glutamine, and supplemented with 2-20% fetal bovine serum (FBS). It is within the skill of one in the art to modify or modulate concentrations of media and/or media supplements as necessary for the cells used. Sera often contain cellular and non-cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), porcine serum, sheep serum, rabbit serum, rat serum (RS), etc. It is also within the scope of the invention that if said recipient MSC are of human origin, the cell culture medium is supplemented with a human serum, preferably of autologous origin. It is understood that sera can be heat-inactivated at 55-65 deg C. if deemed necessary to inactivate components of the complement cascade. Modulation of serum concentrations, withdrawal of serum from the culture medium can also be used to promote survival of one or more desired cell types. Preferably, said recipient MSC will benefit from FBS concentrations of about 2% to about 25%. In another embodiment, the recipient MSC can be expanded in a culture medium of definite composition, in which the serum is replaced by a combination of serum albumin, serum transferrin, selenium, and recombinant proteins including but not limited to insulin, platelet-derived growth factor (PDGF), and basic fibroblast growth factor (bFGF) as known in the art. Many cell culture media already contain amino acids, however some require supplementation prior to culturing of cells. Such amino acids include, but are not limited to, L-alanine, L-arginine, L-aspartic acid, L-asparagine, L cysteine, L-cystine, L-glutamic acid, L-glutamine, L-glycine, and the like. Antimicrobial agents are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone®), ampicilin, gentamicin, bleomycin, hygromacin, kanamycin, mitomycin, etc. Hormones can also be advantageously used in cell culture and include, but are not limited to, D-aldosterone, diethylstilbestrol (DES), dexamethasone, b-estradiol, hydrocortisone, insulin, prolactin, progesterone, somatostatin/human growth hormone (HGH), etc.

Expanded Recipient MSC

Cell expansion is generally carried out over a plurality of passages, wherein each passage comprises a dilution of the cell culture, expansion of the diluted cell culture to a desired population density followed by a subsequent redilution. In one embodiment the recipient MSC may have been expanded prior to use in the method of the present invention. Methods for cell expansion are known in the art. It is particularly preferred that said cells are expanded prior to introducing the nucleic acid construct into the cell. In one embodiment of the method said expansion is carried out by duplication or triplication of said population at least 1, at least 2, at least 3, at least 4, at least 5, at least 10, at least 15 or at least 20 times. In a further embodiment said expansion is carried over at least 1, at least 2, at least 3, at least 4, at least 5, at least 10, at least 15 or at least 20 passages.

The nucleic acid construct is then introduced into the cell. This may be carried out by any means standard in the art.

Methods for inserting exogenous nucleic acids are known in the art. In one embodiment the nucleic acid constructs may be inserted into a DNA vector such as but not limited to viral, plasmid or cosmid vectors. The insertion is generally carried out by means of restriction and ligation of the construct and vector sequences by appropriate enzymatic means. Said enzymes and suitable vectors are known to the person skilled in the art. In one embodiment of the invention said vectors are expression vectors and may themselves comprise of a constitutive promoter, the nucleic acid construct being inserted such that gene expression may be controlled by said promoter. The person skilled in that art, taking into account the host cell to be used is capable of selecting an appropriate vector such that the nucleic acid constructs of the invention when successfully inserted into a host cell will be transcribed and translated such that the host cell constitutively expresses and secretes functional IDO or functional equivalent fragments, variants, and analogs thereof.

The resulting recombinant vector constructs are then introduced into the recipient cell. This may be carried out by any means standard in the art including transformation or transduction, but is preferably carried out by transduction or other means suitable for introduction of a vector into an animal cell. Methods for the transfection of vector nucleic acids include calcium phosphate treatment, viral transduction, nanoparticle bombardment, heat shock, magnetofection, or by the use of commercially available kits or reagents.

It is preferred that the insertion of the nucleic acid construct of the invention into a recipient cell is carried out by means of viral transduction.

Methods for Preparing Immunoregulatory Cells of the Invention

The IDO cells of the invention also have ex-vivo applications in the preparation of immunomodulatory cells suitable for in-vivo therapy of patients in need thereof. Accordingly, in one aspect, the present invention provides methods for the preparation and/or generation of immunomodulatory cells that suppress activation of the immune system and prevent pathological self-reactivity, i.e. an autoimmune disease. In one embodiment said immunomodulatory cells are regulatory T-cells, in a particularly preferred embodiment said immunomodulatory cells are Foxp3+CD4+CD25+ T-reg and/or IL-10/TGFb-producing regulatory Tr1 cells. The immunomodulatory cells prepared and/or generated according to the method of the present invention constitute a further aspect of the instant invention.

In one embodiment said method comprises contacting IDO cells of the invention with blood or components thereof. Said components are most preferably peripheral blood mononuclear cells (PBMC) or peripheral blood leukocytes (PBL).

It is preferred that the ratio of number of IDO cells of the invention to PBL and/or PBMC is between 1:1 and 1:150 respectively. It is further preferred that the ratio of number of IDO cells of the invention to PBL and/or PBMC is between 1:70 and 1:5. It is particularly preferred that the ratio of number of IDO cells of the invention to PBL and/or PBMC is between 1:60 and 1:30. Accordingly, in one embodiment this may be about 1 IDO cell of the invention to every 25 peripheral blood leukocytes or 1 IDO cell of the invention to every 10 peripheral blood mononuclear cells.

In a further embodiment of the method both the agents IL-4 and GM-CSF are used in the method of the invention. It is preferred that the ratio of the concentration of GM-CSF to the concentration of IL-4 is between 5:1 or 1:1 and that the concentrations of each of said agents is between 1 and 2000 IU/ml, it is further preferred that said concentration is between 500 and 1000 IU/ml. Accordingly, in one embodiment this may be about 1000 IU/ml GM-CSF to about 500 IU/ml IL-4.

In said method for preparing and/or generating immunoregulatory cells of the invention, a MSC and/or fibroblast cell population is cultured in vitro with peripheral blood leukocytes in the presence of at least one agent selected from the group consisting of LPS, IL-2, IL-4 and GM-CSF. The culture period is preferably between 1 day and 15 days, and is more preferably between 7 and 10 days. In a further embodiment said culture is carried out for at least 2, at least 4, at least 5, or at least 6 or more days. This co-culturing results in the production of immunomodulatory cells, which can be used for treatment of a subject.

The method(s) for preparing immunoregulatory cells are preferably performed in a temperature and carbon dioxide controlled environment, e.g. in an incubator. The method is preferably preformed at about mammalian body temperature, accounting for regional variations, e.g. 37 degrees centigrade. It is also preferred that the method of the invention is carried out in an environment where carbon dioxide concentration is between 0% and 10% and more preferably between 1% and 5%.

With respect to the intended recipient of the immunomodulatory cells as prepared by the method of the present invention, the MSC and/or fibroblast cells used in said above described method may be of either allogeneic (donor) or autologous (subject) origin. In one embodiment of the method said MSC and/or fibroblast cells are of allogeneic origin.

Preparation of PBL/PBMC

With respect to the intended recipient of the immunomodulatory cells as prepared by the above described method of the present invention, the peripheral blood components used in said method may be of either autologous or allogeneic origin. However it is preferred that they are of autologous origin (i.e. that they were obtained from the subject who subsequently receives the immunomodulatory cells or any treatment, medicament or pharmaceutical composition thereof). Methods for the isolation of PBL/PBMC from whole blood are known in the art and include the use of Ficoll-Hypaque and/or red blood cell lysis procedures or commercially available means such as the LeucoPREP™ cell separation device (Becton Dickinson & Co.) and HISTOPAQUE™ (Sigma Diagnostics) solution.

Method for the Preparation of Antigen Specific Immunomodulatory Cells

The invention also provides methods for the preparation and/or or generation of immunomodulatory cells specific for a chosen antigen or group of antigens (hereinafter also referred to as antigen specific immunomodulatory cells or antigen specific immunomodulatory cells of the invention) and the use of these in the treatment of disease or disorders relating to that antigen or group of antigens. Examples of such antigens are those that play a role in autoimmune diseases, such as, for example, rheumatoid arthritis, Crohn's disease, hypersensitivity reaction Type IV, lupus, psoriasis and other autoimmune disorders known in the art and described elsewhere herein. In one embodiment said antigen specific immunomodulatory cells are regulatory T-cells, in a particularly preferred embodiment said antigen specific immunomodulatory cells are Foxp3+CD4+CD25+ T-reg and/or IL-10/TGFb-producing regulatory Tr1 cells. The antigen specific immunomodulatory cells specific for a chosen antigen or group of antigens prepared and/or generated according to said method of the present invention constitute a further aspect of the instant invention.

Said method comprises contacting IDO cells of the invention with blood or components thereof and a chosen antigen or group of antigens. Said components are most peripheral blood mononuclear cells (PBMC) or peripheral blood leukocytes (PBLS).

In one embodiment said method comprises contacting a MSC and/or fibroblast cell population with peripheral blood leukocytes and a chosen antigen or group of antigens in the presence of at least one agent selected from the group consisting of LPS, IL-2, IL-4 and GM-CSF.

In one embodiment of the method the agent is LPS (gram negative bacterial endotoxin lipopolysacharide). It is preferred that the LPS concentration is between 0.01 and 100 µg/ml, it is further preferred that said concentration is between 1 and 50 µg/ml e.g. about 10 µg/ml.

In one embodiment of the method the agent is IL-2. It is preferred that the IL-2 concentration is between about 0.01 and 1000 IU/ml, it is further preferred that said concentration is up to about 500, up to about 600, up to about 700, up to about 800 or up to about 900 IU/ml.

In an alternative embodiment said agent is either of GM-CSF and IL-4. GM-CSF and IL-4 are both cytokines. It is preferred that the concentration thereof is between 1 and 2000 IU/ml, it is further preferred that said concentration is between 500 and 1000 IU/ml.

In a further embodiment of the method both the agents IL-4 and GM-CSF are used in the method of the invention. It is preferred that the ratio of the concentration of GM-CSF to the concentration of IL-4 is between 5:1 or 1:1 and that the concentrations of each of said agents is between 1 and 2000 IU/ml, it is further preferred that said concentration is between 500 and 1000 IU/ml. Accordingly, in one embodiment this may be about 1000 IU/ml GM-CSF to 500 IU/ml IL-4.

In the method for preparing and/or generating antigen specific immunomodulatory cells, IDO cells of the invention are cultured in vitro with peripheral blood leukocytes and a chosen antigen, group of antigens or cell types expressing and/or presenting said antigen or antigens. Said contact or culture period is preferably between about 2 hours and about 25 days, is more preferably between about 10 and about 18 days more preferably between about 14 and 16 days. In a further embodiment said culture or contact is carried out for at least 10, at least 12, at least 14, or at least 15 or more days. This co-culturing will result in the production of immunomodulatory cells, which can be used for treatment of a subject.

The method(s) of the invention are preferably performed in a temperature and carbon dioxide controlled environment, e.g. in an incubator. The method is preferably preformed at about mammalian body temperature, accounting for regional variations, e.g. 37 degrees centigrade. It is also preferred that the method of the invention is carried out in an environment where carbon dioxide concentration is between 0% and 10% and more preferably between 1% and 5%.

In an alternative embodiment the method for the preparation and/or or generation of antigen specific immunoregulatory cells comprises (a) contacting peripheral blood leukocytes and/or peripheral blood mononuclear cells with a chosen antigen or group of antigens, (b) bringing said cell population into contact with a MSC and/or fibroblast cell population In step (a) of said method for preparing and/or generating antigen specific immunomodulatory cells peripheral blood leukocytes are cultured in vitro in the presence of a chosen antigen, group of antigens or cell types expressing and/or presenting said antigen or antigens. After a culture period of about 2, 4, 6, 12, 24, 48 or more hours, preferably between about 12 to about 24 hours, the cell population of the invention is further co-cultured, optionally after the removal of the antigen, group of antigens or cells carrying said antigen, with the IDO cells of the invention. Said contact or culture period is preferably between about 2 hours and about 25 days, is more preferably between about 10 and about 18 days more preferably between about 14 and 16 days. In a further embodiment said culture or contact is carried out for at least 10, at least 12, at least 14, or at least 15 or more days. This co-culturing will result in the production of immunomodulatory cells, which can be used for treatment of a subject. This co-culturing will result in the production of immunomodulatory cells specific for the chosen antigen, which can be used for treatment of a subject.

The method(s) of the invention are preferably performed in a temperature and carbon dioxide controlled environment, e.g. in an incubator. The method is preferably preformed at about mammalian body temperature, accounting for regional variations, e.g. 37 degrees centigrade. It is also preferred that the method of the invention is carried out in an environment where carbon dioxide Antigen(s)

The antigen used in said methods for the preparation and/or generation of antigen specific immunomodulatory cells may be a chosen antigen, group of antigens or cell types expressing and/or presenting said antigen or antigens. In one embodiment the antigen is selected from a group comprising of: a mixture of autoantigens derived from a patient suffering with autoimmunity, a peptide antigen, a nucleic acid, an altered peptide ligand, a recombinant protein or fragments thereof. In one embodiment said antigens are associated with arthritis (such as but not limited to collagen antigens). In an alternative embodiment said antigens are associated with Celiac Disease (alternatively referred to as cœiac disease, c(o)eliac sprue, non-tropical sprue, endemic sprue, gluten enteropathy or gluten-sensitive enteropathy, and gluten intolerance). Antigens associated with Celiac Disease are members of the gluten family including some forms of prolamins (such as but not limited to antigens of gliadins, hordeins, and/or secalins). In a further embodiment said antigens are associated with multiple sclerosis (such as but not limited to myelin antigens). Methods for the isolation, purification and preparation of such antigens are known to the person skilled in the art.

In a further embodiment contacting the IDO cell of the invention with peripheral blood leukocytes (or components thereof) and optionally a chosen antigen or group of antigens is carried out in the presence of at least one agent selected from the group consisting of LPS, IL-2, IL-4 and GM-CSF.

In one embodiment of the method the agent is LPS (gram negative bacterial endotoxin lipopolysacharide). It is preferred that the LPS concentration is between 0.01 and 100 μg/ml, it is further preferred that said concentration is between 1 and 50 μg/ml e.g. about 10 μg/ml.

In one embodiment of the method the agent is IL-2. It is preferred that the IL-2 concentration is between about 0.01 and 1000 IU/ml, it is further preferred that said concentration is up to about 500, up to about 600, up to about 700, up to about 800 or up to about 900 IU/ml.

In an alternative embodiment said agent is either of GM-CSF and IL-4. GM-CSF and IL-4 are both cytokines. It is preferred that the concentration thereof is between 1 and 2000 IU/ml, it is further preferred that said concentration is between 500 and 1000 IU/ml.

In a further embodiment of the method both the agents IL-4 and GM-CSF are used in the method of the invention. It is preferred that the ratio of the concentration of GM-CSF to the concentration of IL-4 is between 5:1 or 1:1 and that the concentrations of each of said agents is between 1 and 2000 IU/ml, it is further preferred that said concentration is between 500 and 1000 IU/ml. Accordingly, in one embodiment this may be about 1000 IU/ml GM-CSF to 500 IU/ml IL-4.

Cells of the Invention

"IDO cells of the invention", "immunoregulatory cells of the invention" and "antigen specific immunomodulatory cells of the invention" shall be collectively referred to herein as "cells of the invention".

Compositions of the Invention

The present invention also provides a composition comprising of the cells of the invention. Particularly preferred is a cell composition comprising essentially of the cells of the invention. Accordingly in one aspect the present invention provides a composition or population of cells wherein at least about 20%, at least about 30%, at least about 40%, at least about 50%, at least about 60%, at least about 70%, at least about 80%, at least about 90%, at least about 95% or preferably at least about 96%, at least about 97%, at least about 98% or at least about 99% of the cells of said population are cells of the invention. In one embodiment said cell composition is a cell culture and accordingly further comprises suitable medium, buffers, growth factors, nutrients and/or suchlike. Said cell culture may be contained within a suitable vessel and maintained in a constant and suitable environment. Methods for the culture of cells are known in the art.

Use of Cells of the Invention

The cells of the invention can be used for preventing, treating or ameliorating one or more symptoms associated with disease conditions, in particular those in which modulation of a subject's immune system is beneficial. These include but are not limited to including, autoimmune diseases, inflammatory disorders, and immunologically mediated diseases. Said use constitutes an additional aspect of the present invention.

Thus, in another aspect, the cells of the invention are used as a medicament. In a particular embodiment, medicaments comprising of the cells of the invention may be used for inducing transplantation tolerance, or for treating, and thereby alleviating, symptoms of autoimmune or inflammatory disorders, or immunologically mediated diseases including rejection of transplanted organs and tissues, in a subject suffering from any of said disorders or diseases. Thus, the cells of the invention can be used to therapeutically or prophylactically treat and thereby alleviate symptoms of immune, autoimmune or inflammatory disorders in a subject suffering from any of said disorders or to alleviate symptoms of immunologically mediated diseases in a subject suffering from said diseases. The cells of the invention are of use in the treatment of autoimmune disease, inflammatory disorder or immunological mediated disease. Illustrative, non-limiting examples of said diseases and disorders which can be treated are those previously listed under heading "Definitions". In a particular embodiment, said inflammatory disease is a chronic inflammatory disease, such as, e.g., Celiac Disease, Multiple Sclerosis, Psoriasis, IBD or RA. In another aspect, the present invention relates to the use of the cells of the invention for the preparation of a medicament for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Thus, the invention further refers to the use of the cells of the invention for the preparation of a medicament for suppressing the immune response, or for inducing transplantation tolerance, or for treating autoimmune diseases, or for treating inflammatory disorders. Examples of said autoimmune diseases and inflammatory diseases have been previously mentioned. In a particular embodiment, disease is an inflammatory disease, such as a chronic inflammatory disease, e.g., Celiac Disease, Multiple Sclerosis, Psoriasis, IBD or RA.

Use of Antigen Specific Immunomodulatory Cells

The invention also provides the use of the antigen specific immunomodulatory cells, prepared and/or generated according to the methods of the invention in the treatment of diseases and disorders related to said chosen antigen or groups of antigens by administration of said antigen specific immunomodulatory cells to a subject, most preferably the subject from which the peripheral blood leukocytes were obtained.

Thus, in another aspect, said antigen specific immunomodulatory cells are used as a medicament. In a particular embodiment, medicaments comprising of the antigen specific immunomodulatory cells as described herein may be used for the treatment of diseases and disorders related to said chosen antigen or groups of antigens. Thus, the antigen specific immunomodulatory cells can be used to therapeutically or prophylactically treat and thereby alleviate symptoms of autoimmune or inflammatory disorders in a subject suffering from any of said disorders or to alleviate symptoms of immunologically mediated diseases in a subject suffering from said diseases. The antigen specific immunomodulatory cells of the present invention are of use in the treatment of autoimmune disease, inflammatory disorder or immunological mediated disease. Illustrative, non-limiting examples of said diseases and disorders which can be treated are those previously listed under heading "Definitions". In a particular embodiment, said inflammatory disease is a chronic inflammatory disease, such as, e.g., Celiac Disease, Multiple Sclerosis, Psoriasis, IBD or RA. In another aspect, the present invention relates to the use of the antigen specific cells of the invention for the preparation of a medicament for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Thus, the invention further refers to the use of the antigen specific immunomodulatory cells as described herein for the preparation of a medicament for suppressing the immune response associated with said antigen(s). Examples of said autoimmune diseases and inflammatory diseases have been previously mentioned. In a particular embodiment, disease is an inflammatory disease, such as a chronic inflammatory disease, e.g., Celiac Disease, Multiple Sclerosis, Psoriasis, IBD or RA.

Pharmaceutical Compositions

The present invention provides pharmaceutical compositions for the treatment, prophylaxis, and amelioration of one or more symptoms associated with a disorder in which modulation of a subject's immune system is beneficial. These include autoimmune diseases, inflammatory disorders, and immunologically mediated diseases including rejection of transplanted organs and tissues.

Thus, in another aspect, the invention relates to a pharmaceutical composition, hereinafter referred to as the pharmaceutical composition of the invention, comprising cells of the invention and a pharmaceutical carrier. Combinations of two or more of said type of cells are included within the scope of the pharmaceutical compositions provided by the instant invention.

The pharmaceutical composition of the invention comprises a prophylactically or therapeutically effective amount of one or more prophylactic or therapeutic agents (i e, cells of the invention), and a pharmaceutical carrier. Suitable pharmaceutical carriers are known in the art and are preferably those approved by a regulatory agency of the US Federal or a state government or listed in the US or European Pharmacopeia, or other generally recognized pharmacopeia for use in animals, and more particularly in humans. The term "carrier" refers to a diluent, adjuvant, excipient, or vehicle with which the therapeutic agent is administered. The composition, if desired, can also contain minor amounts of pH buffering agents. Examples of suitable pharmaceutical carriers are described in "Remington's Pharmaceutical Sciences" by E W Martin. Such compositions will contain a prophylactically or therapeutically effective amount of a prophylactic or therapeutic agent preferably in purified form, together with a suitable amount of carrier so as to provide the form for proper administration to the subject. The formulation should suit the mode of administration. In a preferred embodiment, the pharmaceutical compositions are sterile and in suitable form for administration to a subject, preferably an animal subject, more preferably a mammalian subject, and most preferably a human subject.

The pharmaceutical composition of the invention may be in a variety of forms. These include, for example, solid, semi-solid, and liquid dosage forms, such as lyophilized preparations, liquids solutions or suspensions, injectable and infusible solutions, etc. The preferred form depends on the intended mode of administration and therapeutic application.

The administration of the cells of the invention, or the pharmaceutical composition comprising same, to the subject in need thereof can be carried out by conventional means. In a particular embodiment, said cell population is administered to the subject by a method which involves transferring the cells to the desired tissue, either in vitro (e.g., as a graft prior to implantation or engrafting) or in vivo, to the subject tissue directly. The cells can be transferred to the desired tissue by any appropriate method, which generally will vary according to the tissue type. For example, cells can be transferred to a graft by bathing the graft (or infusing it) with culture medium containing the cells. Alternatively, the cells can be seeded onto the desired site within the tissue to establish a population. Cells can also be administered systemically e.g. by means of infusion of a cell suspension. Cells can be transferred to sites in vivo using devices such as catheters, trocars, cannulae, stents (which can be seeded with the cells), etc.

The cell populations and pharmaceutical compositions of the invention can be used in a combination therapy. In a specific embodiment, the combination therapy is administered to a subject with an inflammatory disorder that is refractory to one or more anti-inflammatory agents. In another embodiment, the combination therapy is used in conjunction with other types of anti-inflammatory agents including, but not limited to, nonsteroidal anti-inflammatory drugs (NSAIDs), steroidal anti-inflammatory drugs, beta-agonists, anticholingeric agents, and methyl xanthines. Examples of NSAIDs include, but are not limited to, Ibuprofen, celecoxib, diclofenac, etodolac, fenoprofen, Indomethacin, ketoralac, oxaprozin, nabumentone, suhndac, tolmentin, rofecoxib, naproxen, ketoprofen, nabumetone, etc. Such NSAIDs function by inhibiting a cyclooxygenase enzyme (e.g., COX-I and/or COX-2). Examples of steroidal anti-inflammatory drugs include, but are not limited to, glucocorticoids, dexamethasone, cortisone, hydrocortisone, prednisone, prednisolone, triamcinolone, azulf[iota]dine, and eicosanoids such as thromboxanes, and leukotrienes. Monoclonal antibodies, such as Infliximab, can also be used.

In accordance with the above embodiment, the combination therapies of the invention can be used prior to, concurrently or subsequent to the administration of such anti-inflammatory agents. Further, such anti-inflammatory agents do not encompass agents characterized herein as lymphoid tissue inducers and/or immunomodulatory agents.

In another aspect, the present invention relates to the use of the cells of the invention for the preparation or manufacture of a pharmaceutical composition or medicament for preventing, treating or ameliorating one or more symptoms associated with disorders in which modulation of a subject's immune system is beneficial, including, but not limited to, autoimmune diseases, inflammatory disorders, and immunologically mediated diseases including rejection of transplanted organs and tissues. Thus, the invention further refers to the use of the cells of the invention for the preparation or manufacture of a pharmaceutical composition or medicament for suppressing the immune response, or for inducing transplantation tolerance, or for treating autoimmune diseases, or for treating inflammatory disorders. Examples of said autoimmune diseases and inflammatory diseases include but are not limited to Coeliac Disease, Multiple Sclerosis, Psoriasis, Inflammatory Bowel Disease (IBD) and Rheumatoid Arthritis (RA).

KITS The present invention further relates to kits of use in the preparation and/or use of cells of the invention. In one embodiment said kit comprises i) IDO cells of the invention and ii) at least one agent selected from the group consisting of LPS, IL-2, IL-4 and GM-CSF.

In one embodiment said agent is LPS (gram negative bacterial endotoxin lipopolysacharide). It is preferred that the LPS concentration is between 0.01 and 100 µg/ml, it is further preferred that said concentration is between 1 and 50 µg/ml e.g. about 10 µg/ml.

In one embodiment of the method the agent is IL-2. It is preferred that the IL-2 concentration is between about 0.01 and 1000 IU/ml, it is further preferred that said concentration is up to about 500, up to about 600, up to about 700, up to about 800 or up to about 900 IU/ml.

In an alternative embodiment said agent is either of GM-CSF and IL-4. It is preferred that the concentration thereof is between 1 and 2000 µg/ml, it is further preferred that said concentration is between 500 and 1000 µg/ml.

In a further embodiment both the agents IL-4 and GM-CSF are provided in said kit of the invention, either as a mixture or in separate containers. It is preferred that the ratio of the concentration of GM-CSF to the concentration of IL-4 is between 5:1 or 1:1 and that the concentrations of each of said agents is between 1 and 2000 µg/ml, it is further preferred that said concentration is between 500 and 1000 µg/ml. Accordingly, in one embodiment this may be about 1000 µg/ml GM-CSF to about 500 µg/ml IL-4.

In a further embodiment said kit further comprises iii) one or more antigens or cell types expressing and/or presenting said one or more antigens. In a further embodiment, said kits of the invention may comprise iv) instructions for use in the preparation and/or generation of immunomodulatory cells.

In a further embodiment the present invention provides kits of use in treating a subject with the cells of the invention. Said kit comprises i) cells of the invention and ii) a device for administering said cells. Said devices include but are not limited to syringes, injection devices, catheters, trocars, cannulae and stents.

In a further embodiment, all kits of the invention may further comprise instructions for use in the treatment of a subject.

USES The nucleic acid constructs, cells comprising said constructs, methods for making said cells, immunoregulatory cells prepared using said cells as well as compositions and kits comprising of the cells of the invention may be used in preventing, treating or ameliorating one or more symptoms associated with disease conditions, in particular those in which modulation of a subject's immune system is beneficial. These include but are not limited to, autoimmune diseases, inflammatory disorders, and immunologically mediated diseases such as but not limited to Coeliac Disease, Multiple Sclerosis, Psoriasis, Inflammatory Bowel Disease (IBD) and Rheumatoid Arthritis (RA). Said use constitutes an additional aspect of the present invention.

EXAMPLES

Example 1

Preparation of IDO Construct

In order to clone the IDO fragment, reverse transcription of cDNA from mRNA obtained from adipose derived stem cells (hereinafter also referred to as ASCs) stimulated with IFN-gamma was carried out. IFN-gamma stimulation results in the production of IDO in ASC. 15.000 adipose derived stem cells/sqcm were plated into a 75 sqm tissue culture plate and stimulated with 3 ng/ml IFN-g for 48 hours. RNA was obtained using Invitrogen's TRIzol reagent according to manufacturers specifications. cDNA was transcribed using Invitrogen's Superscript II kit according to manufacturers specifications.

The cDNA obtained was amplified by means of PCR using the following amplification primers:

```
Forward primer:
AGGAGCAGACTACAAGAATGGCAC      (SEQ ID NO: 3)

Reverse primer:
GTTTGTGGCTCTGTTACAATGGG       (SEQ ID NO: 4)
```

PCR was carried out at an annealing temperature of 56.4 degrees centigrade. The Invitrogen™ High Fidelity Expand kit was used for carrying out the PCR. The amplified nucleic acid was isolated by means of gel electrophoresis and subcloned using the Invitrogen™ TOPO II cloning kit according to manufacturer's instructions. Several clones were sequenced and correct clones CEL-P907 GBp were used for further cloning. SEQ ID NO: 1 was inserted into a vector (see SEQ ID NO: 2). Briefly, the IDO gene sequenced was excised using standard restriction enzymes such as Not I and BamHI and was subsequently cloned into the proprietary vector pRV IRES neo as detailed in WO 2005061721. The 5 transfection processes and subsequent generation of retroviral supernatant was performed using Polyethylenimine (1 vol PEI: 2 vol DNA). Viral supernatants were then used in the transduction of adipose derived stem cells. See WO 2005061721 for further details.

IDO Activity

ASCs transduced with the IDO vector, and subsequently constitutively expressing IDO are hereinafter referred to as hASC-IDO+ cells. As a comparison ASCs carrying a siRNA silencer of the IDO gene (hASC-IDOsi) were made as well as 15 control ASC transformed with the appropriate empty vector (hASC-empty). The IDO activity of these clones was assessed by HPLC in both resting conditions and after IFN-gamma stimulation (3 ng/ml) at different time points. As expected, hASC-empty cells only led to Kynurenine (Kyn) production when stimulated with IFN-gamma. Importantly, hASC-IDO+ cells constitutively accumulated Kyn into the medium. This activity was further induced by IFNgamma treatment. hASC-IDOsi cells showed a striking reduction in Kyn concentration after stimulation with IFN-gamma, indicating that silencing of IDO was very efficient (FIG. 1).

Immunosuppressive Effects of Cells

Figure 3:
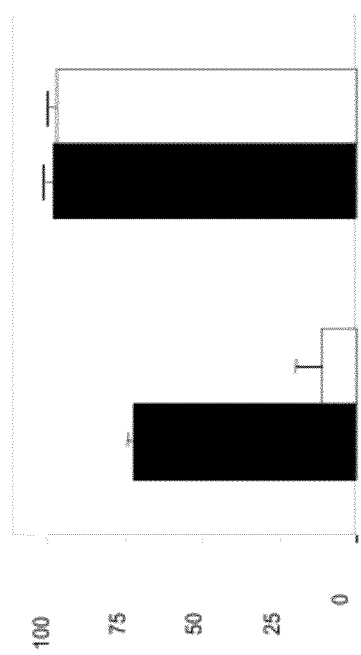
FIG. 3 shows the % of PBMC inhibition on the Y-axis by hASC-empty (the black and white left hand bars) and hASC-IDO+ (the black and white right hand bars). The black bars show unstimulated cells, the white bars show ASCs that had been pre-stimulated with IFN-gamma.

In order to further establish that constitutive expression of IDO enhances immunosuppression PBMCs were stimulated in the presence of hASC-empty or hASC-IDO+ cells at a suboptimal 1:50 ratio and PBMC proliferation was determined. As shown in FIG. 2, hASC-IDO+ cells significantly increased inhibition compared to control cells. Next, the effect of silencing IDO activity on hASC-mediated immunosuppression was analyzed. Accordingly, PBMCs were stimulated in the presence of hASC-empty or hASC-IDOsi cells at a ratio 1:25 and PBMC proliferation was determined. Notably, hASC-IDOsi cells showed a strikingly reduced capacity to inhibit PBMC proliferation (FIG. 2). Furthermore, IFN-gamma neutralization, while preventing immunosuppression by hASC-empty, had no effect on hASC-IDO+ (FIG. 3). All together, these data indicate that induction of IDO activity plays an essential role in the mechanism of immunosuppression mediated by hASCs.

Example 2

Regulatory T-Cell Generation

ASCs contacted with peripheral blood mononuclear cells under suitable conditions results in the generation of regulatory T cells. Such methods are disclosed in WO2007039150. In order to demonstrate that the hASCs-IDO+ are superior at generating regulatory T cells, the population of regulatory T cells generated was compared to that when generated using stem cells derived from adipose using standard means (i.e. without the IDO construct) hereinafter also referred to as hASCs; as well as those generated using ASCs carrying a specific siRNA to silence IDO expression (hASC-IDOsi). As a control, a clone with the appropriate empty vector was generated and used to transform ASC (hASC-empty). hASCs, hASCs-IDO+, hASCs-IDOsi and hASCs-IDO empty, were plated in a 24 well plate and cultured for 24 hours. PBMCs were activated with the Pan T cell Activation kit (micro beads loaded with anti-CD3, anti-CD2 and anti-CD28) and cultured with or without hASCs (ratio ASCs:PBMCs 1:25) in contact system. At day 5 cells were harvested for FACS analysis. Cells were stained with antibodies against CD25, CD4, CD3 labelled with PE, PerCP and APC respectively, in order to detect the population of regulatory T cells (Treg) (described as CD3+CD4+CD25+++). After washing, cells were fixed and acquired using a FACScalibur (BD Bioscience). 50×103 events were acquired and CellQuest-pro software was used for acquisition and analysis. CALIBRITE beads (BD Bioscience) were used prior to each assay to calibrate the cytometer. Data were analyzed over gated lymphocytes (based on forward and side scatter properties).

Figure 4:
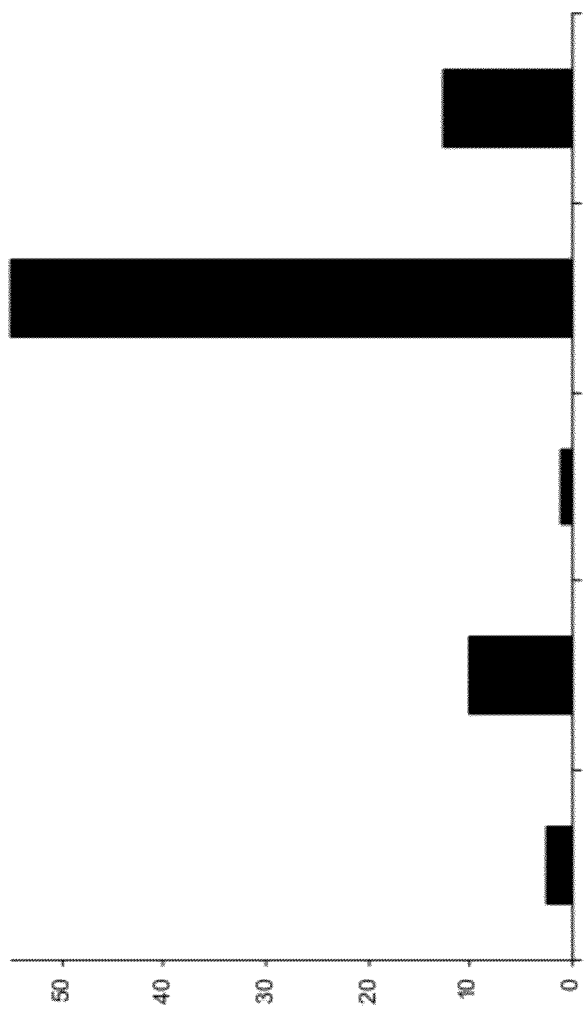
FIG. 4 provides a bar chart showing the % of CD25 positive cells in the population of CD4 cells generated using various adipose derived stem cell types. The first cell population on the left was generated without ASCs, the second from the left was generated by hASCs-empty, the middle population was generated using hASCs-IDOsi, the fourth from the left by hASC-IDO+ and the population furthest on the right by normal ASCs.

As shown in FIG. 4, when PBMCs are stimulated and cultured without the presence of ASCs, the percentage of Treg population within the total CD4 cells (CD3+CD4+CD25+++) is 2.4%. However in the presence of hASCs and ASCIDOempty the percentage reached is around 10-15%. The co-culture of PBMCs together with hASCs-IDO+ (hASC constitutively expressing IDO), lead to the generation of 50% of Treg cells in the CD4 total population. As a negative control of this experiment the hASC-IDOsi that do not express IDO enzyme was used. This clone induced less than 2% of Treg population inside the CD4 cell subset. Accordingly it can be concluded that the constitutive expression of IDO in the hASC increases the generation of regulatory T-cells (CD3+CD4+CD25+++).

In order to confirm this observation the experiment was repeated as described with the addition of 100 UI/ml of IL-2 and culture over 7 days. After 7 days of culture cells were harvested by centrifugation and pelleting and were analysed by mean of flow cytometry (FACS). Results of the FACS analysis for individual wells are provided in FIG. 3, illustrating that using the (IDO CLONE) 19.5% of cells were CD4+CD25 bright as opposed to 8.94% using (SIL) and 16.1% (WT). This is further illustrated in FIG. 4 which shows the comparative means of all wells in each group. These cells were confirmed as being regulatory T-cells by means of intracellular FOXP3.

Results of the experiment confirms that the percentage of Treg found in the co-cultures where ASC present the silenced gene was lower than the cell generated when IDO activity was present.

Figure 5:
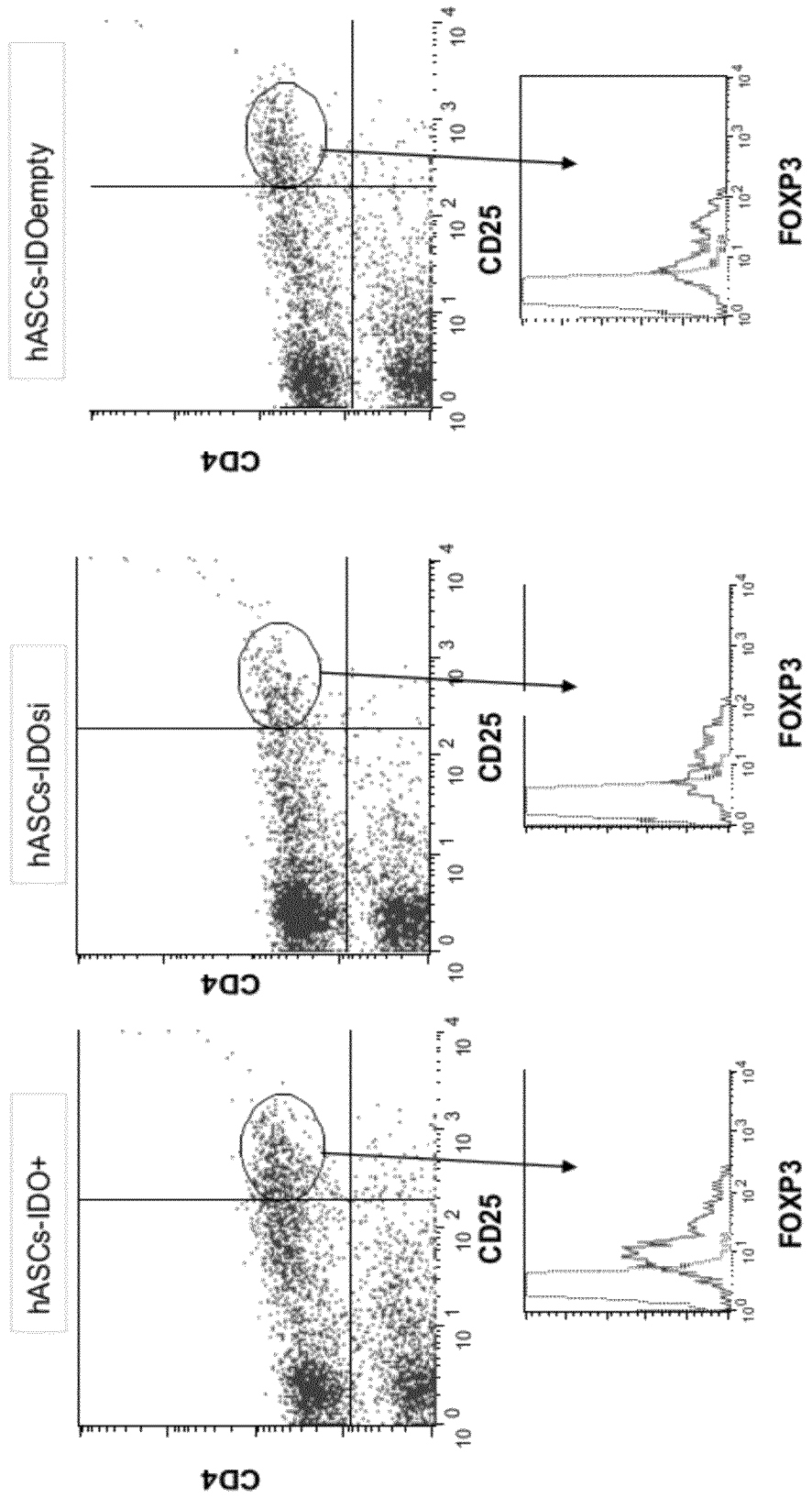
FIG. 5 provides a representative dot plot of three of the conditions analysed in the second part of Experiment 2. The plot on the left provides the FACS analysis (CD4/CD25/FOXP3) of a PBMC co-cultures with the ASC with the constitutive gene, the centre plot provides the FACS results of a well wherein the ASC present the silenced gene and the plot on the right provides the control having an empty vector.

FIG. 5 provides a representative dot plot of three of the conditions analysed in the second part of Experiment 2. The plot on the left provides the FACS analysis (CD4/CD25/FOXP3) of a PBMC co-cultures with the ASC with the constitutive gene, the centre plot provides the FACS results of a well wherein the ASC present the silenced gene and the plot on the right provides the control having an empty vector.

Figure 6:
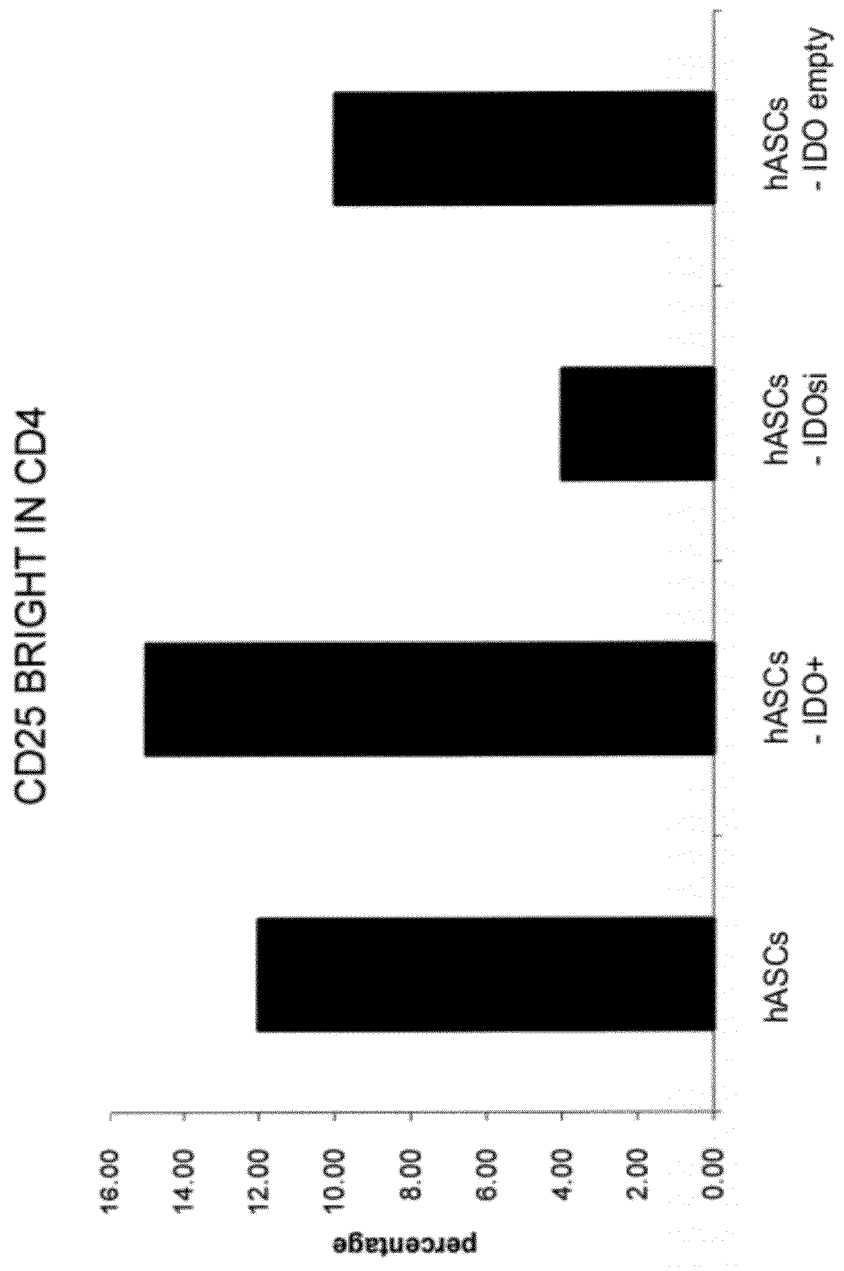
FIG. 6 shows the average percentage of regulatory T-cells in each of the co-cultures.

FIG. 6 shows the average percentage of regulatory T-cells in each of the co-cultures. It can be seen that IDO constitutive induces more Tregs than IDO empty and IDO silenced. It can also been seen ASCs generate approximately the same amount of Tregs as the IDO empty

The invention claimed is:

1. An in vitro method for the preparation and/or generation of CD4+CD25+FoxP3+ T-regulatory cells comprising contacting mesenchymal stem cells with peripheral blood mononuclear cells or peripheral blood leukocytes, wherein the mesenchymal stem cells comprise exogenous nucleic acid constructs comprising indoleamine 2,3-dioxygenase (IDO) nucleic acid sequences operably linked to a constitutive promoter that drives constitutive expression of IDO in the mesenchymal stem cells.

2. A method according to claim 1 wherein said contacting is carried out in the presence of at least one agent selected from the group consisting of LPS, IL-2, IL-4 and GM-CSF.

3. An in vitro method for the preparation and/or generation of CD4+CD25+FoxP3+ T-regulatory cells specific for an antigen, comprising contacting mesenchymal stem cells with peripheral blood mononuclear cells or peripheral blood leukocytes in the presence of said antigen, wherein the mesenchymal stem cells comprise exogenous nucleic acid constructs comprising indoleamine 2,3-dioxygenase (IDO) nucleic acid sequences operably linked to a constitutive promoter that drives constitutive expression of IDO in the mesenchymal stem cells.

* * * * *

SEQUENCE LISTING

```
<160> NUMBER OF SEQ ID NOS: 6

<210> SEQ ID NO 1
<211> LENGTH: 1246
<212> TYPE: DNA
<213> ORGANISM: Homo sapiens

<400> SEQUENCE: 1
ggatcctaac tcgagatgcc accatggcac acgctatgga aaactcctgg acaatcagta      60
aagagtacca tattgatgaa gaagtgggct ttgctctgcc aaatccacag gaaaatctac     120 ctgatttta  taatgactgg atgttcattg ctaaacatct gcctgatctc atagagtctg     180
gccagcttcg agaaagagtt gagaagttaa acatgctcag cattgatcat ctcacagacc     240
```

| | |
|---|---|
| acaagtcaca gcgccttgca cgtctagttc tgggatgcat caccatggca tatgtgtggg | 300 |
| gcaaaggtca tggagatgtc cgtaaggtct tgccaagaaa tattgctgtt ccttactgcc | 360 |
| aactctccaa gaaactggaa ctgcctccta ttttggttta tgcagactgt gtcttggcaa | 420 |
| actggaagaa aaaggatcct aataagcccc tgacttatga aacatggac gttttgttct | 480 |
| catttcgtga tggagactgc agtaaaggat tcttcctggt ctctctattg gtggaaatag | 540 |
| cagctgcttc tgcaatcaaa gtaattccta ctgtattcaa ggcaatgcaa atgcaagaac | 600 |
| gggacacttt gctaaaggcg ctgttggaaa tagcttcttg cttggagaaa gcccttcaag | 660 |
| tgtttcacca aatccacgat catgtgaacc caaaagcatt tttcagtgtt cttcgcatat | 720 |
| atttgtctgg ctggaaaggc aacccccagc tatcagacgg tctggtgtat gaagggttct | 780 |
| ggaagaccc aaaggagttt gcaggggca gtgcaggcca agcagcgtc tttcagtgct | 840 |
| ttgacgtcct gctgggcatc cagcagactg ctggtggagg acatgctgct cagttcctcc | 900 |
| aggacatgag aagatatatg ccaccagctc acaggaactt cctgtgctca ttagagtcaa | 960 |
| atccctcagt ccgtgagttt gtcctttcaa aaggtgatgc tggcctgcgg gaagcttatg | 1020 |
| acgcctgtgt gaaagctctg gtctccctga ggagctacca tctgcaaatc gtgactaagt | 1080 |
| acatcctgat tcctgcaagc cagcagccaa aggagaataa gacctctgaa gacccttcaa | 1140 |
| aactggaagc caaaggaact ggaggcactg atttaatgaa tttcctgaag actgtaagaa | 1200 |
| gtacaactga gaaatccctt ttgaaggaag gttaattgaa ttctga | 1246 |

<210> SEQ ID NO 2
<211> LENGTH: 7054
<212> TYPE: DNA
<213> ORGANISM: Homo sapiens

<400> SEQUENCE: 2

| | |
|---|---|
| ggccggccga agtggtttaa acgttgacat tgattattga ctagttatta atagtaatca | 60 |
| attacggggt cattagttca tagcccatat atggagttcc gcgttacata acttacggta | 120 |
| aatggcccgc ctggctgacc gcccaacgac ccccgcccat tgacgtcaat aatgacgtat | 180 |
| gttcccatag taacgccaat agggactttc cattgacgtc aatgggtgga gtatttacgg | 240 |
| taaactgccc acttggcagt acatcaagtg tatcatatgc caagtacgcc ccctattgac | 300 |
| gtcaatgacg gtaaatggcc cgcctggcat tatgcccagt acatgacctt atgggacttt | 360 |
| cctacttggc agtacatcta cgtattagtc atcgctatta ccatggtgat gcggttttgg | 420 |
| cagtacatca atgggcgtgg atagcggttt gactcacggg gatttccaag tctccacccc | 480 |
| attgacgtca atgggagttt gttttggcac caaaatcaac gggactttcc aaaatgtcgt | 540 |
| aacaactccg ccccattgac gcaaatgggc ggtaggcgtg tacggtggga ggtctatata | 600 |
| agcagagctc aataaaagag cccacaaccc ctcactcggg cgccagtcc tccgattgac | 660 |
| tgagtcgccc gggtacccgt gtatccaata aaccctcttg cagttgcatc cgacttgtgg | 720 |
| tctcgctgtt ccttgggagg gtctcctctg agtgattgac tacccgtcag cggggggtctt | 780 |
| tcatttgggg gctcgtccgg gatcgggaga cccctgccca gggaccaccg acccaccacc | 840 |
| gggaggtaag ctggccagca acttatctgt gtctgtccga ttgtctagtg tctatgactg | 900 |
| attttatgcg cctgcgtcgg tactagttag ctaactagct ctgtatctgg cggacccgtg | 960 |
| gtggaactga cgagttcgga acacccggcc gcaaccctgg gagacgtccc agggacttcg | 1020 |
| ggggccgttt ttgtggcccg acctgagtcc aaaaatcccg atcgttttgg actctttggt | 1080 |
| gcacccccct tagaggaggg atatgtggtt ctggtaggag acgagaacct aaaacagttc | 1140 |

```
ccgcctccgt ctgaattttt gctttcggtt tgggaccgaa gccgcgccgc gcgtcttgtc    1200
tgctgcagca tcgttctgtg ttgtctctgt ctgactgtgt ttctgtattt gtctgaaaat    1260
atgggcccgg ccagactgt  taccactccc ttaagtttga ccttaggtca ctggaaagat    1320
gtcgagcgga tcgctcacaa ccagtcggta gatgtcaaga agagacgttg ggttaccttc    1380
tgctctgcag aatggccaac ctttaacgtc ggatggccgc gagacggcac ctttaaccga    1440
gacctcatca cccaggttaa gatcaaggtc ttttcacctg gcccgcatgg acacccagac    1500
caggtcccct acatcgtgac ctgggaagcc ttggcttttg accccctcc  ctgggtcaag    1560 cccttttgtac accctaagcc tccgcctcct cttcctccat ccgccccgtc tctccccctt   1620
gaacctcctc gttcgacccc gcctcgatcc tcccttatc  cagccctcac tccttctcta    1680
ggcgccccca tatggccata tgagatcttg agttaactaa gcatgctagt cgaggctcga    1740
caaagttaag taatagttcc ctctctccaa gctcacttac aggcggatcc taactcgaga    1800
tgccaccatg gcacacgcta tggaaaactc tggacaatc  agtaaagagt accatattga    1860
tgaagaagtg ggctttgctc tgccaaatcc acaggaaaat ctacctgatt tttataatga    1920
ctggatgttc attgctaaac atctgcctga tctcatagag tctggccagc ttcgagaaag    1980
agttgagaag ttaaacatgc tcagcattga tcatctcaca gaccacaagt cacagcgcct    2040
tgcacgtcta gttctgggat gcatcaccat ggcatatgtg tggggcaaag gtcatggaga    2100
tgtccgtaag gtcttgccaa gaaatattgc tgttccttac tgccaactct ccaagaaact    2160
ggaactgcct cctatttttgg tttatgcaga ctgtgtcttg gcaaactgga agaaaaagga    2220
tcctaataag cccctgactt atgagaacat ggacgttttg ttctcatttc gtgatggaga    2280
ctgcagtaaa ggattcttcc tggtctctct attggtggaa atagcagctg cttctgcaat    2340
caaagtaatt cctactgtat tcaaggcaat gcaaatgcaa gaacgggaca cttttgctaaa   2400 ggcgctgttg gaaatagctt cttgcttgga gaaagccctt caagtgtttc accaaatcca    2460
cgatcatgtg aacccaaaag cattttttcag tgttcttcgc atatatttgt ctggctggaa   2520
aggcaacccc cagctatcag acggtctggt gtatgaaggg ttctgggaag acccaaagga    2580
gtttgcaggg ggcagtgcag gccaaagcag cgtcttttcag tgctttgacg tcctgctggg   2640
catccagcag actgctggtg gaggacatgc tgctcagttc ctccaggaca tgagaagata    2700
tatgccacca gctcacagga acttcctgtg ctcattagag tcaaatccct cagtccgtga    2760
gtttgtcctt tcaaaaggtg atgctggcct gcgggaagct tatgacgcct gtgtgaaagc    2820
tctggtctcc ctgaggagct accatctgca aatcgtgact aagtacatcc tgattcctgc    2880
aagccagcag ccaaaggaga ataagacctc tgaagaccct tcaaaactgg aagccaaagg    2940
aactggaggc actgatttaa tgaatttcct gaagactgta agaagtacaa ctgagaaatc    3000
ccttttgaag gaaggttaat tgaattctga tttaaatctc cgcgggcccg ggatcgatcc    3060
gcccctctcc ctccccccc  cctaacgtta ctggccgaag ccgcttggaa taaggccggt    3120
gtgcgtttgt ctatatgtta ttttccacca tattgccgtc ttttggcaat gtgagggccc    3180
ggaaacctgg ccctgtcttc ttgacgagca ttcctagggg tctttcccct ctcgccaaag    3240
gaatgcaagg tctgttgaat gtcgtgaagg aagcagttcc tctggaagct tcttgaagac    3300
aaacaacgtc tgtagcgacc ctttgcaggc agcggaaccc cccacctggc gacaggtgcc    3360
tctgcggcca aaagccacgt gtataagata cacctgcaaa ggcggcacaa ccccagtgcc    3420
acgttgtgag ttggatagtt gtggaaagag tcaaatggct ctcctcaagc gtattcaaca    3480
```

```
aggggctgaa ggatgcccag aaggtacccc attgtatggg atctgatctg gggcctcggt   3540
gcacatgctt tacatgtgtt tagtcgaggt taaaaaaacg tctaggcccc ccgaaccacg   3600
gggacgtggt tttcctttga aaaacacgat gataatatgg ccacaaccat gattgaacaa   3660
gatggattgc acgcaggttc tccggccgct tgggtggaga ggctattcgg ctatgactgg   3720
gcacaacaga caatcggctg ctctgatgcc gccgtgttcc ggctgtcagc gcaggggcgc   3780
ccggttcttt ttgtcaagac cgacctgtcc ggtgccctga tgaactgca ggacgaggca   3840
gcgcggctat cgtggctggc cacgacgggc gttccttgcg cagctgtgct cgacgttgtc   3900
actgaagcgg gaagggactg gctgctattg ggcgaagtgc cggggcagga tctcctgtca   3960
tctcaccttg ctcctgccga aaagtatcc atcatggctg atgcaatgcg gcggctgcat   4020
acgcttgatc cggctacctg cccattcgac caccaagcga acatcgcat cgagcgagca   4080
cgtactcgga tggaagccgg tcttgtcgat caggatgatc tggacgaaga gcatcagggg   4140
ctcgcgccag ccgaactgtt cgccaggctc aaggcgcgca tgcccgacgg cgaggatctc   4200
gtcgtgaccc atggcgatgc ctgcttgccg aatatcatgg tggaaaatgg ccgcttttct   4260
ggattcatcg actgtggccg ctgggtgtg gcggaccgct atcaggacat agcgttggct   4320
acccgtgata ttgctgaaga gcttggcggc gaatgggctg accgcttcct cgtgctttac   4380
ggtatcgccg ctcccgattc gcagcgcatc gccttctatc gccttcttga cgagttcttc   4440
tgaagcggcc gccagcacag tggtcgacga taaaataaaa gatttatttt agtctccaga   4500
aaaaggggg aatgaaagac cccacctgta ggtttggcaa gctagcttaa gtaacgccat   4560
tttgcaaggc atggaaaaat acataactga gaatagagaa gttcagatca aggtcaggaa   4620
cagatggaac agctgaatat gggccaaaca ggatatctgt ggtaagcagt tcctgccccg   4680
gctcagggcc aagaacagat ggaacagctg aatatgggcc aaacaggata tctgtggtaa   4740
gcagttcctg ccccggctca gggccaagaa cagatggtcc ccagatgcgg tccagccctc   4800
agcagtttct agagaaccat cagatgtttc caggtgcccc aaggacctg aaatgaccct   4860
gtgccttatt tgaactaacc aatcagttcg cttctcgctt ctgttcgcgc gcttctgctc   4920
cccgagctca ataaaagagc ccacaacccc tcactcgggg cgccagtcct ccgattgact   4980
gagtcgcccg ggtacccgtg tatccaataa accctcttgc agttgcatcc gacttgtggt   5040
ctcgctgttc cttgggaggg tctcctctga gtgattgact acccgtcagc gggggtcttt   5100
cattcacatg cagcatgtat caaaattaat ttggtttttt tcttaagta tttacattaa   5160
atggccatag ttgcattaat gaatcggcca acgcgcgggg agaggcggtt tgcgtattgg   5220
cgctcttccg cttaattaa gcatggagca aaaggccagc aaaaggccag gaaccgtaaa   5280
aaggccgcgt tgctggcgtt tttccatagg ctccgccccc ctgacgagca tcacaaaaat   5340
cgacgctcaa gtcagaggtg gcgaaacccg acaggactat aaagatacca ggcgtttccc   5400
cctggaagct ccctcgtgcg ctctcctgtt ccgaccctgc cgcttaccgg atacctgtcc   5460
gcctttctcc cttcgggaag cgtggcgctt tctcatagct cacgctgtag gtatctcagt   5520
tcggtgtagg tcgttcgctc caagctgggc tgtgtgcacg aacccccgt tcagcccgac   5580
cgctgcgcct tatccggtaa ctatcgtctt gagtccaacc cggtaagaca cgacttatcg   5640
ccactggcag cagccactgg taacaggatt agcagagcga ggtatgtagg cggtgctaca   5700
gagttcttga agtggtggcc taactacggc tacactagaa ggacagtatt tggtatctgc   5760
gctctgctga agccagttac cttcggaaaa agagttggta gctcttgatc cggcaaacaa   5820
accaccgctg gtagcggtgg tttttttgtt tgcaagcagc agattacgcg cagaaaaaaa   5880
```

-continued

| | |
|---|---|
| ggatctcaag aagatccttt gatcttttct acggggtctg acgctcagtg aacgaaaac | 5940 |
| tcacgttaag ggattttggt catgagatta tcaaaaagga tcttcaccta gatccttta | 6000 |
| aattaaaaat gaagttttaa atcaatctaa agtatatatg agtaaacttg gtctgacagt | 6060 |
| taccaatgct taatcagtga ggcacctatc tcagcgatct gtctatttcg ttcatccata | 6120 |
| gttgcctgac tccccgtcgt gtagataact acgatacggg agggcttacc atctggcccc | 6180 |
| agtgctgcaa tgataccgcg agacccacgc tcaccggctc cagatttatc agcaataaac | 6240 |
| cagccagccg gaagggccga gcgcagaagt ggtcctgcaa ctttatccgc ctccatccag | 6300 |
| tctattaatt gttgccggga agctagagta agtagttcgc cagttaatag tttgcgcaac | 6360 |
| gttgttgcca ttgctacagg catcgtggtg tcacgctcgt cgtttggtat ggcttcattc | 6420 |
| agctccggtt cccaacgatc aaggcgagtt acatgatccc ccatgttgtg caaaaaagcg | 6480 |
| gttagctcct tcggtcctcc gatcgttgtc agaagtaagt tggccgcagt gttatcactc | 6540 |
| atggttatgg cagcactgca taattctctt actgtcatgc catccgtaag atgcttttct | 6600 |
| gtgactggtg agtactcaac caagtcattc tgagaatagt gtatgcggcg accgagttgc | 6660 |
| tcttgcccgg cgtcaatacg ggataatacc gcgccacata gcagaacttt aaaagtgctc | 6720 |
| atcattggaa aacgttcttc ggggcgaaaa ctctcaagga tcttaccgct gttgagatcc | 6780 |
| agttcgatgt aacccactcg tgcacccaac tgatcttcag catcttttac tttcaccagc | 6840 |
| gtttctgggt gagcaaaaac aggaaggcaa aatgccgcaa aaaagggaat aagggcgaca | 6900 |
| cggaaatgtt gaatactcat actcttcctt tttcaatatt attgaagcat ttatcagggt | 6960 |
| tattgtctca tgagcggata catatttgaa tgtatttaga aaaataaaca aatagggg tt | 7020 |
| ccgcgcacat ttccccgaaa agtgccacct acgt | 7054 |

<210> SEQ ID NO 3
<211> LENGTH: 24
<212> TYPE: DNA
<213> ORGANISM: Homo sapiens

<400> SEQUENCE: 3
aggagcagac tacaagaatg gcac                                            24

<210> SEQ ID NO 4
<211> LENGTH: 23
<212> TYPE: DNA
<213> ORGANISM: Homo sapiens

<400> SEQUENCE: 4
gtttgtggct ctgttacaat ggg                                             23

<210> SEQ ID NO 5
<211> LENGTH: 403
<212> TYPE: PRT
<213> ORGANISM: Homo sapiens

<400> SEQUENCE: 5

Met Ala His Ala Met Glu Asn Ser Trp Thr Ile Ser Lys Glu Tyr His
1               5                   10                  15

Ile Asp Glu Glu Val Gly Phe Ala Leu Pro Asn Pro Gln Glu Asn Leu
            20                  25                  30

Pro Asp Phe Tyr Asn Asp Trp Met Phe Ile Ala Lys His Leu Pro Asp
        35                  40                  45

Leu Ile Glu Ser Gly Gln Leu Arg Glu Arg Val Glu Lys Leu Asn Met

```
                50             55              60
Leu Ser Ile Asp His Leu Thr Asp His Lys Ser Gln Arg Leu Ala Arg
 65                  70                  75                  80

Leu Val Leu Gly Cys Ile Thr Met Ala Tyr Val Trp Gly Lys Gly His
                 85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Asp Pro Asn Lys Tyr Val Asn
    130                 135                 140

Thr Gly Asn Met Asp Val Leu Phe Ser Phe Arg Asp Gly Asp Cys Ser
145                 150                 155                 160

Lys Gly Phe Phe Leu Val Ser Leu Leu Val Glu Ile Ala Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Glu Ile Ala Ser Cys Leu Glu
        195                 200                 205

Lys Ala Leu Gln Val Phe His Gln Ile His Asp His Val Asn Pro Lys
    210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
            260                 265                 270

Phe Asp Val Leu Leu Gly Ile Gln Gln Thr Ala Gly Gly His Ala
        275                 280                 285

Ala Gln Phe Leu Gln Asp Met Arg Arg Tyr Met Pro Pro Ala His Arg
    290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
                325                 330                 335

Lys Ala Leu Val Ser Leu Arg Ser Tyr His Leu Gln Ile Val Thr Lys
            340                 345                 350

Tyr Ile Leu Ile Pro Ala Ser Gln Gln Pro Lys Glu Asn Lys Thr Ser
        355                 360                 365

Glu Asp Pro Ser Lys Leu Glu Ala Lys Gly Thr Gly Thr Asp Leu
    370                 375                 380

Met Asn Phe Leu Lys Thr Val Arg Ser Thr Thr Glu Lys Ser Leu Leu
385                 390                 395                 400

Lys Glu Gly

<210> SEQ ID NO 6
<211> LENGTH: 1560
<212> TYPE: DNA
<213> ORGANISM: Homo sapiens

<400> SEQUENCE: 6
aatttctcac tgcccctgtg ataaactgtg gtcactggct gtggcagcaa ctattataag    60
atgctctgaa aactcttcag acactgaggg gcaccagagg agcagactac aagaatggca   120
```

```
-continued cacgctatgg aaaactcctg gacaatcagt aaagagtacc atattgatga agaagtgggc      180
tttgctctgc caaatccaca ggaaaatcta cctgattttt ataatgactg gatgttcatt      240
gctaaacatc tgcctgatct catagagtct ggccagcttc gagaaagagt tgagaagtta      300
aacatgctca gcattgatca tctcacagac cacaagtcac agcgccttgc acgtctagtt      360
ctgggatgca tcaccatggc atatgtgtgg ggcaaaggtc atggagatgt ccgtaaggtc      420
ttgccaagaa atattgctgt tccttactgc caactctcca agaaactgga actgcctcct      480
attttggttt atgcagactg tgtcttggca aactggaaga aaaaggatcc taataagtat      540
gtaaacactg ggaacatgga cgttttgttc tcatttcgtg atggagactg cagtaaagga      600
ttcttcctgg tctctctatt ggtggaaata gcagctgctt ctgcaatcaa agtaattcct      660
actgtattca aggcaatgca aatgcaagaa cgggacactt tgctaaaggc gctgttggaa      720
atagcttctt gcttggagaa agcccttcaa gtgtttcacc aaatccacga tcatgtgaac      780
ccaaaagcat tttcagtgt tcttcgcata tatttgtctg gctggaaagg caaccccag       840 ctatcagacg gtctggtgta tgaagggttc tgggaagacc caaaggagtt tgcaggggc      900 agtgcaggcc aaagcagcgt ctttcagtgc tttgacgtcc tgctgggcat ccagcagact      960
gctggtggag gacatgctgc tcagttcctc caggacatga gaagatatat gccaccagct      1020
cacaggaact tcctgtgctc attagagtca aatccctcag tccgtgagtt tgtcctttca      1080
aaaggtgatg ctggcctgcg ggaagcttat gacgcctgtg tgaaagctct ggtctccctg      1140
aggagctacc atctgcaaat cgtgactaag tacatcctga ttcctgcaag ccagcagcca      1200
aaggagaata agacctctga agaccttca aaactggaag ccaaaggaac tggaggcact      1260
gatttaatga atttcctgaa gactgtaaga agtacaactg agaaatccct tttgaaggaa      1320
ggttaatgta acccaacaag agcacatttt atcatagcag agacatctgt atgcattcct      1380
gtcattaccc attgtaacag agccacaaac taatactatg caatgtttta ccaataatgc      1440
aatacaaaag acctcaaaat acctgtgcat ttcttgtagg aaaacaacaa aaggtaatta     1500
tgtgtaatta tactagaagt tttgtaatct gtatcttatc attggaataa aatgacattc      1560
```